US012194251B2

(12) United States Patent
Tavallaei et al.

(10) Patent No.: US 12,194,251 B2
(45) Date of Patent: Jan. 14, 2025

(54) SYSTEM AND METHOD FOR DEVICE STEERING, TRACKING, AND NAVIGATION OF DEVICES FOR INTERVENTIONAL PROCEDURES

(71) Applicant: MAGELLAN BIOMEDICAL INC., Scarborough (CA)

(72) Inventors: Mohammad Ali Tavallaei, Scarborough (CA); Emily Man-Sheun Lam, North York (CA); James Jiewen Zhou, Markham (CA); Graham A. Wright, Toronto (CA)

(73) Assignee: MAGELLAN BIOMEDICAL INC., Richmond Hill (CA)

( * ) Notice: Subject to any disclaimer, the term of this patent is extended or adjusted under 35 U.S.C. 154(b) by 774 days.

(21) Appl. No.: 17/052,108

(22) PCT Filed: May 1, 2019

(86) PCT No.: PCT/US2019/030142
§ 371 (c)(1),
(2) Date: Oct. 30, 2020

(87) PCT Pub. No.: WO2019/213215
PCT Pub. Date: Nov. 7, 2019

(65) Prior Publication Data
US 2021/0052854 A1  Feb. 25, 2021

Related U.S. Application Data

(60) Provisional application No. 62/803,708, filed on Feb. 11, 2019, provisional application No. 62/799,473, (Continued)

(51) Int. Cl.
*A61M 25/01* (2006.01)
*A61M 25/00* (2006.01)
(Continued)

(52) U.S. Cl.
CPC .... *A61M 25/0147* (2013.01); *A61M 25/0074* (2013.01); *A61M 25/0136* (2013.01);
(Continued)

(58) Field of Classification Search
CPC .......... A61M 25/0147; A61M 25/0074; A61M 25/0136; A61M 25/09041; A61M 2025/015; A61M 2025/0079
See application file for complete search history.

(56) References Cited

U.S. PATENT DOCUMENTS

| 4,960,411 A | 10/1990 | Buchbinder |
| 5,143,085 A | 9/1992 | Wilson |

(Continued)

FOREIGN PATENT DOCUMENTS

| CN | 105934212 A | 9/2016 |
| EP | 3 653 105 A1 | 5/2020 |

(Continued)

OTHER PUBLICATIONS

International Preliminary Report on Patentability for Application No. PCT/US2019/030142, mailed on Nov. 12, 2020, 9 pages.
(Continued)

*Primary Examiner* — Jason E Flick
*Assistant Examiner* — Adam J. Cermak
(74) *Attorney, Agent, or Firm* — Merchant & Gould P.C.

(57) ABSTRACT

A steering device and navigation system for interventional procedures. Included are devices, systems, and methods that incorporate a steering device which consists of an expandable structure that can be controlled to spread out within the vessel lumen, or cardiac chamber, and may apply circumferential force to the tissue. This structure, once spread out, can anchor relative to the anatomy and provides support for an internal catheter through a set of strings connected to the internal catheter. The internal catheter is configured to allow
(Continued)

an interventional device, such as a guidewire or catheter, to pass through it. Using the strings that are connected to actuation mechanisms within the device's handle, the internal catheter can be manipulated to allow controlling the position of a device that runs within it or is connected to it and can be used for the purpose of navigation of devices and obtaining measurements from known positions.

22 Claims, 39 Drawing Sheets

Related U.S. Application Data filed on Jan. 31, 2019, provisional application No. 62/665,046, filed on May 1, 2018.

(51) Int. Cl.
*A61M 25/04* (2006.01)
*A61M 25/09* (2006.01)

(52) U.S. Cl.
CPC ............... *A61M 25/09041* (2013.01); *A61M 2025/0166* (2013.01); *A61M 25/04* (2013.01); *A61M 2205/583* (2013.01); *A61M 2210/125* (2013.01)

(56) References Cited

U.S. PATENT DOCUMENTS

| | | | | |
|---|---|---|---|---|
| 5,318,525 | A | 6/1994 | West et al. | |
| 5,324,284 | A | 6/1994 | Imran | |
| 5,325,845 | A | 7/1994 | Adair | |
| 5,327,889 | A | 7/1994 | Imran | |
| 5,343,853 | A | 9/1994 | Komi | |
| 5,415,633 | A | 5/1995 | Lazarus et al. | |
| 5,509,900 | A * | 4/1996 | Kirkman | A61M 25/04 606/198 |
| 5,676,653 | A | 10/1997 | Taylor et al. | |
| 5,681,280 | A | 10/1997 | Rusk et al. | |
| 5,879,295 | A * | 3/1999 | Li | A61B 18/1492 607/125 |
| 6,066,125 | A | 5/2000 | Webster, Jr. | |
| 6,231,551 | B1 * | 5/2001 | Barbut | A61B 17/12172 606/198 |
| 6,280,413 | B1 * | 8/2001 | Clark | A61F 2/013 604/103.08 |
| 6,500,167 | B1 | 12/2002 | Webster, Jr. | |
| 6,936,015 | B2 | 8/2005 | Esashi et al. | |
| 7,169,160 | B1 | 1/2007 | Middleman et al. | |
| 7,226,467 | B2 * | 6/2007 | Lucatero | A61B 17/1227 606/191 |
| 7,269,453 | B2 | 9/2007 | Mogul | |
| 7,412,274 | B2 | 8/2008 | Mejia | |
| 8,066,664 | B2 | 11/2011 | LaDuca et al. | |
| 8,083,667 | B2 | 12/2011 | Cooper et al. | |
| 8,114,073 | B2 | 2/2012 | Whayne et al. | |
| 8,133,171 | B2 | 3/2012 | Barry et al. | |
| 8,137,333 | B2 | 3/2012 | Saadat et al. | |
| 8,353,850 | B2 | 1/2013 | Ressemann et al. | |
| 8,663,304 | B2 | 3/2014 | Wallace et al. | |
| 8,702,625 | B2 | 4/2014 | Ayala et al. | |
| 9,125,683 | B2 | 9/2015 | Farhangnia et al. | |
| 9,126,020 | B2 | 9/2015 | Farhangnia et al. | |
| 9,226,648 | B2 | 1/2016 | Saadat et al. | |
| 9,314,208 | B1 * | 4/2016 | Altmann | A61B 5/6858 |
| 9,364,167 | B2 | 6/2016 | Vertikov | |
| 9,492,623 | B2 * | 11/2016 | Kapadia | A61M 5/427 |
| 9,526,401 | B2 | 12/2016 | Saadat et al. | |
| 9,636,480 | B2 | 5/2017 | Sevensma | |
| 9,724,195 | B2 * | 8/2017 | Goodwin | A61F 2/2466 |
| 10,092,172 | B2 | 10/2018 | Peh et al. | |
| 10,575,911 | B2 * | 3/2020 | Mylonas | A61B 34/70 |
| 10,595,994 | B1 | 3/2020 | Christianson et al. | |
| 11,304,769 | B2 | 4/2022 | Cooper et al. | |
| 11,311,699 | B2 * | 4/2022 | Weisz | A61M 25/0136 |
| 2003/0109889 | A1 | 6/2003 | Mercereau | A61B 17/221 606/127 |
| 2004/0087975 | A1 * | 5/2004 | Lucatero | A61B 17/0487 606/139 |
| 2005/0216044 | A1 | 9/2005 | Hong | |
| 2006/0100544 | A1 * | 5/2006 | Ayala | A61M 25/09 600/585 |
| 2006/0264980 | A1 | 11/2006 | Khairkhahan et al. | |
| 2007/0113700 | A1 | 5/2007 | Khajepour et al. | |
| 2007/0173812 | A1 | 7/2007 | Bonan et al. | |
| 2007/0239197 | A1 * | 10/2007 | Dubey | A61B 5/1076 606/198 |
| 2009/0149716 | A1 | 6/2009 | Diao et al. | |
| 2010/0179540 | A1 | 7/2010 | Marczyk et al. | |
| 2011/0071490 | A1 * | 3/2011 | Kassab | A61M 25/0133 604/533 |
| 2011/0098805 | A1 | 4/2011 | Dwork et al. | |
| 2011/0112524 | A1 * | 5/2011 | Stern | A61B 18/1485 606/41 |
| 2011/0196410 | A1 | 8/2011 | Besselink et al. | |
| 2011/0238039 | A1 * | 9/2011 | Leonard | A61L 29/16 604/508 |
| 2011/0251509 | A1 * | 10/2011 | Beyhan | A61B 17/12136 600/529 |
| 2012/0323174 | A1 | 12/2012 | Shih | |
| 2013/0041314 | A1 | 2/2013 | Dillon | |
| 2013/0245742 | A1 | 9/2013 | Norris | |
| 2015/0238314 | A1 * | 8/2015 | Bortlein | A61M 25/0082 623/2.11 |
| 2016/0287840 | A1 * | 10/2016 | Jiang | A61M 25/0147 |
| 2016/0339208 | A1 * | 11/2016 | Kanemasa | A61M 25/0147 |
| 2017/0290595 | A1 * | 10/2017 | Miles | A61B 17/12022 |
| 2017/0296266 | A1 | 10/2017 | Salahieh et al. | |
| 2018/0028314 | A1 | 2/2018 | Ekvall et al. | |
| 2018/0028787 | A1 * | 2/2018 | McNiven | A61M 25/0026 |
| 2018/0049803 | A1 | 2/2018 | Solis | |
| 2018/0146925 | A1 | 5/2018 | Mogul | |
| 2018/0243536 | A1 | 8/2018 | Von Segesser | |
| 2019/0008360 | A1 | 1/2019 | Peh et al. | |
| 2019/0009061 | A1 | 1/2019 | Tran et al. | |
| 2019/0047705 | A1 | 2/2019 | Diao et al. | |
| 2019/0374293 | A1 * | 12/2019 | Larkin | A61B 34/32 |
| 2020/0015832 | A1 | 1/2020 | Levins et al. | |
| 2020/0061340 | A1 * | 2/2020 | Mixter | A61B 8/4466 |
| 2020/0155804 | A1 * | 5/2020 | von Oepen | A61F 2/2439 |
| 2020/0170701 | A1 | 6/2020 | O'Keefe et al. | |
| 2021/0153884 | A1 * | 5/2021 | Casey | A61B 17/22 |
| 2021/0154010 | A1 | 5/2021 | Schneider et al. | |
| 2021/0162177 | A1 * | 6/2021 | Weisz | A61M 25/0136 |
| 2021/0186547 | A1 * | 6/2021 | Kassab | A61M 25/008 |
| 2021/0244553 | A1 * | 8/2021 | Wiehn | A61F 2/07 |
| 2021/0322166 | A1 * | 10/2021 | von Oepen | A61F 2/9524 |
| 2021/0361428 | A1 * | 11/2021 | Dixon | A61F 2/2466 |
| 2022/0152357 | A1 | 5/2022 | Tani | A61M 25/008 |
| 2022/0287860 | A1 * | 9/2022 | Sumanasinghe | A61F 2/962 |
| 2022/0296367 | A1 * | 9/2022 | Hoang | A61F 2/2433 |
| 2023/0065020 | A1 * | 3/2023 | Jiang | A61M 25/0147 |
| 2024/0042597 | A1 | 2/2024 | Tavallaei et al. | |

FOREIGN PATENT DOCUMENTS

| | | |
|---|---|---|
| JP | 2009-500052 A | 1/2009 |
| JP | 2015-057093 A | 3/2015 |
| JP | 2015-513926 A | 5/2015 |
| JP | 2013-529109 A | 8/2015 |
| JP | 2017-077480 A | 4/2017 |
| WO | WO 2015/085220 A1 | 6/2015 |
| WO | WO 2019/213215 A1 | 11/2019 |
| WO | WO 2022/125655 A1 | 6/2022 |

OTHER PUBLICATIONS

PCT International Search Report for PCT/US2019/030142, mailed Aug. 23, 2019, 4 pages.

(56) References Cited

OTHER PUBLICATIONS

PCT Written Opinion of the ISA for PCT/US2019/030142, mailed Aug. 23, 2019, 7 pages.
CN Office Action for CN 201980029400.6, dated Jul. 10, 2022 with English Translation, 13 pages.
PCT International Search Report for PCT/US2021/062391, mailed Feb. 23, 2023, 2 pages.
PCT Written Opinion of the ISA for PCT/US2021/062391 mailed Feb. 23, 2022, 5 pages.
International Search Report and Written Opinion for Application No. PCT/US24/11044 mailed May 30, 2024.
Extended European Search Report for Application No. 21904326.2 mailed Oct. 23, 2024.

\* cited by examiner

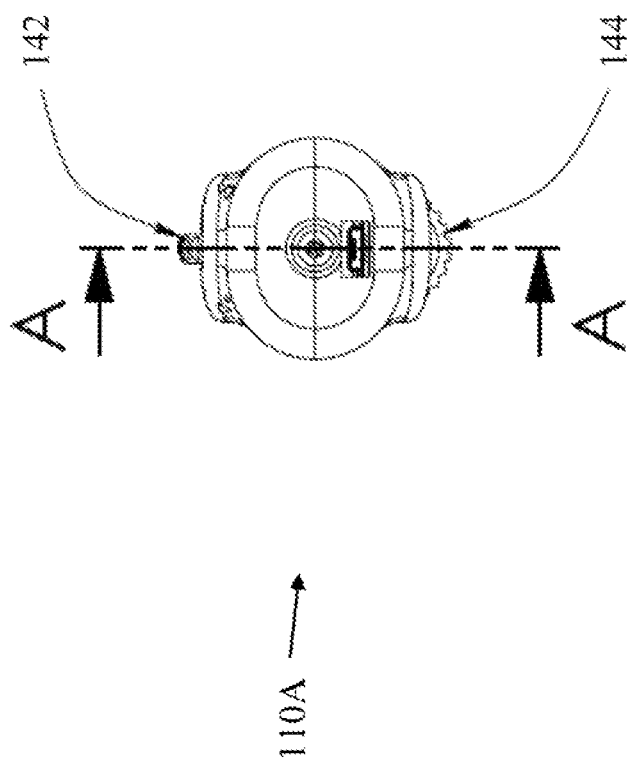

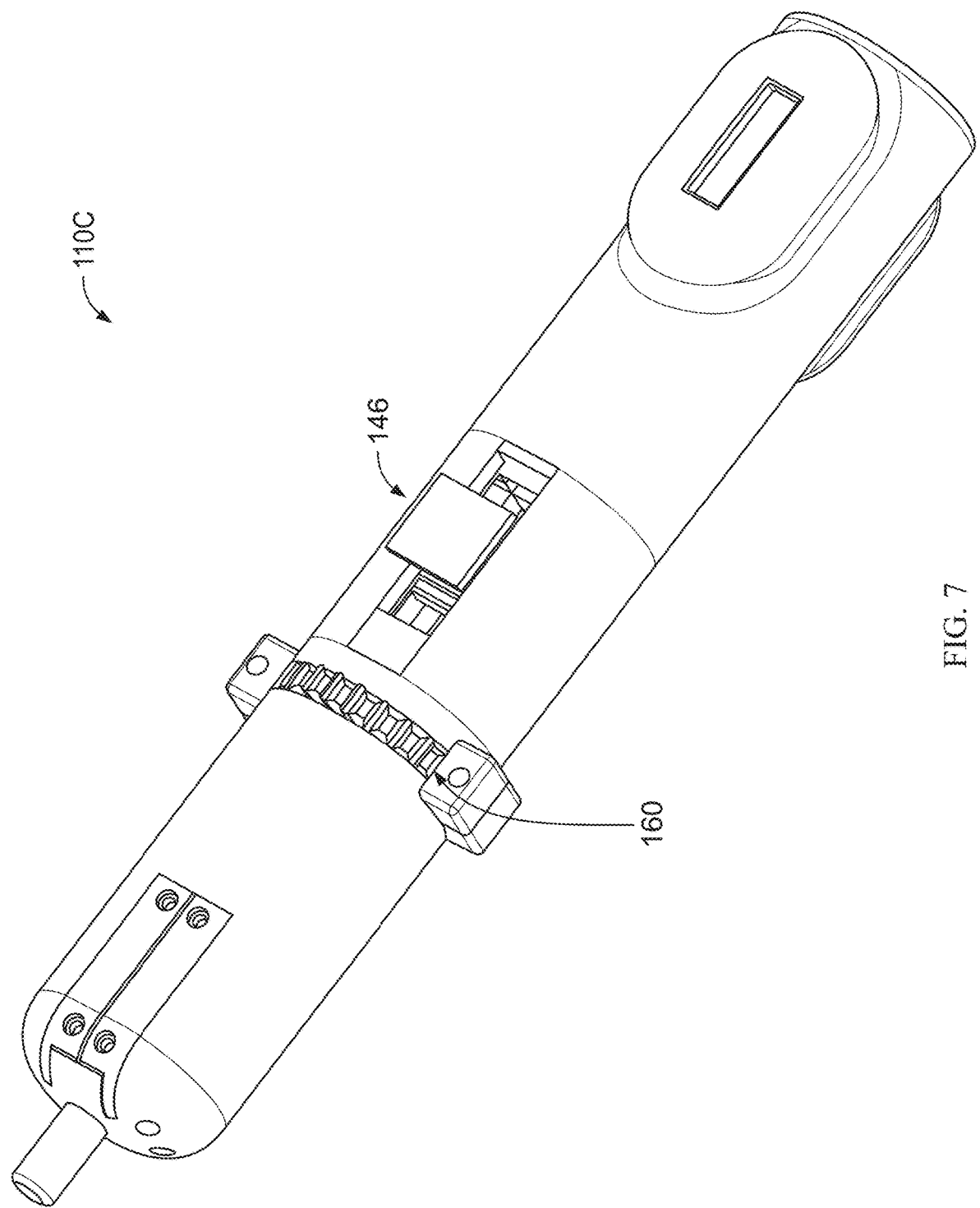

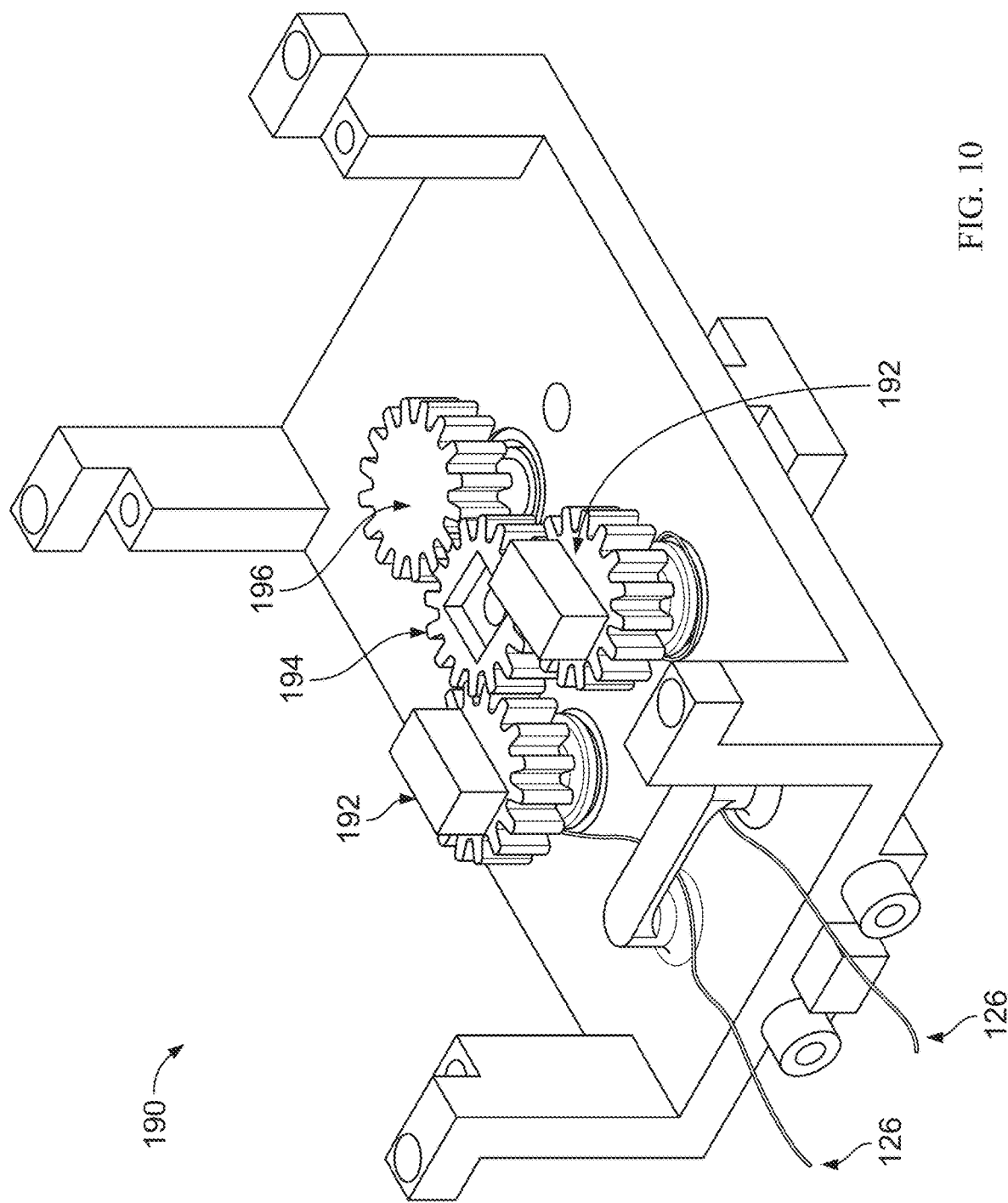

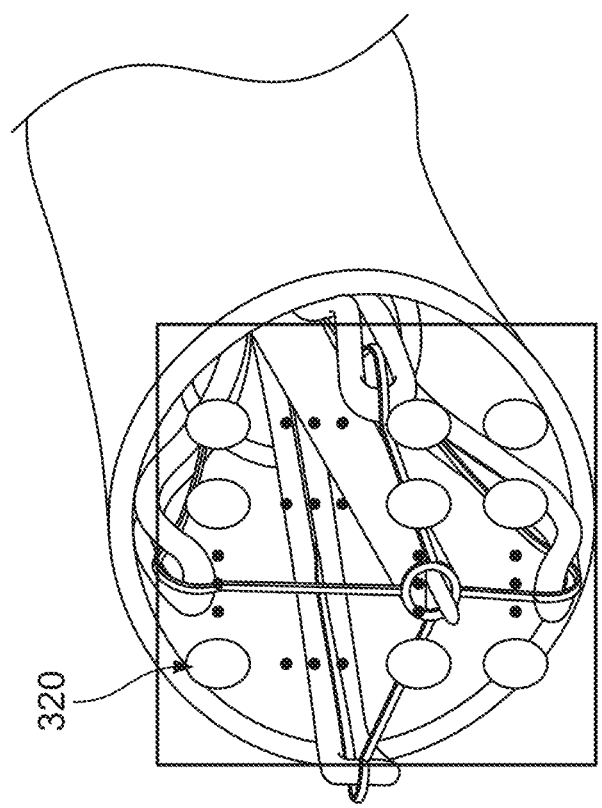

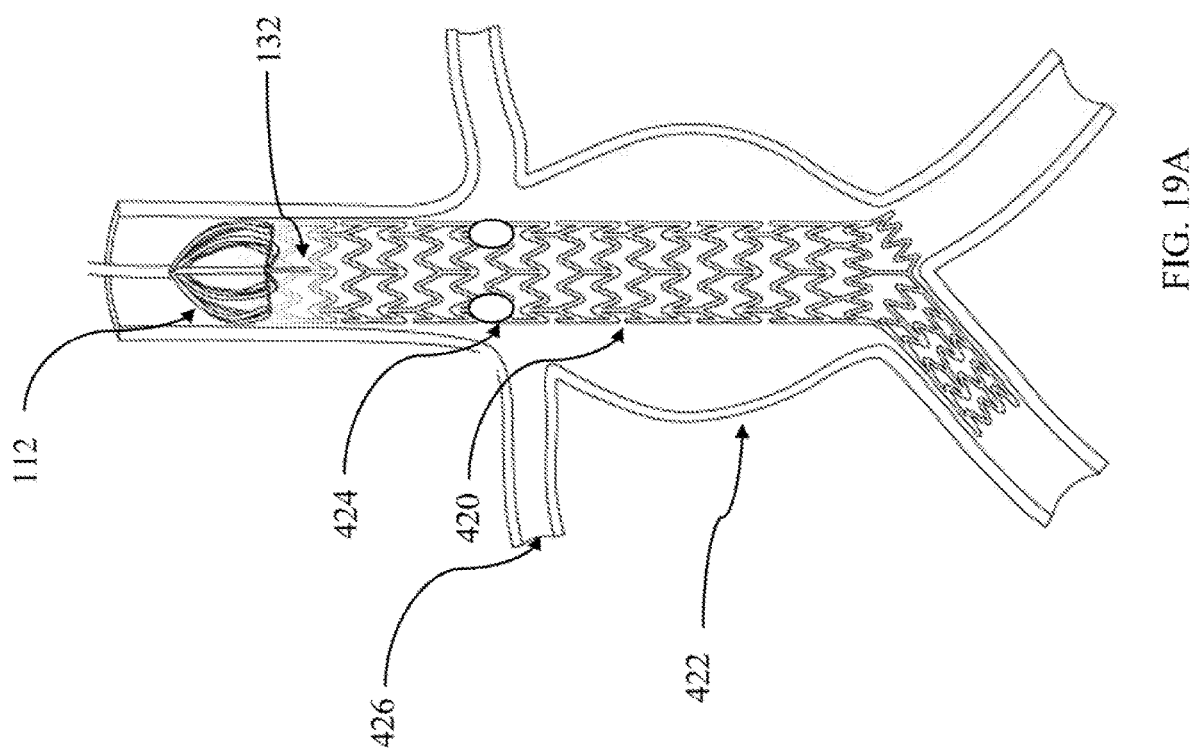

SYSTEM AND METHOD FOR DEVICE STEERING, TRACKING, AND NAVIGATION OF DEVICES FOR INTERVENTIONAL PROCEDURES

CROSS REFERENCE TO RELATED APPLICATIONS

The present application is a National Phase entry of PCT Application No. PCT/US2019/030142, filed on May 1, 2019, which claims priority to US Provisional Patent Application No. 62/665,046, filed on May 1, 2018, U.S. Provisional Patent Application No. 62/799,473, filed on Jan. 31, 2019, and U.S. Provisional Patent Application No. 62/803,708, filed on Feb. 11, 2019, each of which is hereby fully incorporated herein by reference in its entirety.

TECHNICAL FIELD

The present disclosure relates to steering of interventional devices, such as guidewires, catheters, and needles, and more particularly, to steering the tip of an interventional device using strings. Further, the disclosure relates to minimally invasive imaging of human tissue and particularly for the use of this imaging information for diagnostic purposes or for guiding interventional procedures. Further, the disclosure relates to steering and tracking of interventional devices for cardiovascular procedures, and more particularly to control and navigation of interventional devices for cardiac and endovascular interventions.

BACKGROUND

Conventional guidewires, or catheters, are extremely flexible elongate members that can be manipulated from outside the body with typically two degrees of freedom ("DOF"). Generally, the two DOF are axial translation, or push-pull, and axial rotation. Most endovascular interventions require the use of guidewires to allow navigation to desired targets or for passing through obstacles. Given the limitations in navigating the tip of the device through manipulation of the wire from outside the patient's body, an endovascular interventionalist invests most of the procedure time for navigating the guidewire or catheter.

A wide range of cardiovascular procedures are currently performed minimally invasively using a percutaneous approach with minimally invasive devices. Such procedures may be either for diagnostic purposes, by making relevant measurements within or from the relevant target, or they are for therapeutic purposes by means of physical interaction with the tissue to change its form or function or to replace or repair it. All such procedures rely on the use of guidewires and flexible elongated structures, that are generally referred to as catheters.

Conventional guidewires are long, flexible and thin devices that are introduced into a lumen of the body. In conventional guidewire systems, having two DOF, the operator uses axial and radial manipulation on the shaft to navigate the tip of these guidewires to the target locations. To facilitate navigation, and for safety reasons, these wires are very flexible and their shape inside the patient is governed by the shape and geometry of the vessels. The ability to steer conventional guidewires is limited by the mechanical impact of the vessel geometry on the guidewire shape and, additionally, having only two DOF for guidewire manipulation. A further limitation is that these procedures are conventionally guided with x-ray fluoroscopic imaging which provides limited visual feedback as it only provides 2D projection images with limited resolution. Because of these limitations, one of the main challenges during a cardiovascular or endovascular intervention procedure is guidewire manipulation and navigation.

Catheters are generally long thin tubes that are introduced into the vasculature percutaneously and are then guided to the desired anatomical target of interest. These devices are generally manipulated remotely from outside the patient body, by means of push-pull or rotation of the device. Some catheters also have a deflectable tip that may be deflected through actuation of a plunger or knob on the device's handle. These procedures are generally guided with 2D projection x-ray imaging.

While for all procedures it is important to accurately and reliably control the position, shape, and orientation of the device relative to the anatomy, there are several inherent technical limitations that hinder these preferences: the devices are extremely flexible; they are manipulated remotely from outside the patient body; the device's position is effected by its mechanical engagement with the dynamically moving anatomical structures which is difficult to characterize or predict; the friction and mechanical engagement of the device with the anatomy makes it difficult to control or estimate the force at the tip of the device; and it is difficult to visualize or accurately estimate the relative position of the device in relation to the anatomy.

To address such limitations, various attempts have been made to modify the design of such devices (i.e., guidewires and catheters) by adding active and passive mechanisms to the wires to enhance their steering capability. A common approach has been to add tip steering capability by integrating within the device a pull-wire which is connected to its tip.

In addition to adding a pull-wire, tip steering conventionally requires coupling a main catheter shaft comprising higher hardness material with the distal tip comprising lower hardness material. This variance in material composition ensures that manipulating the string manipulates the distal tip primarily. By applying tension on the pull-wire—which is parallel but offset relative the main axis of the device—bending of the distal end relative to the main shaft can be achieved. This approach is broadly used for steerable catheters and steerable guidewires in general and allows for three DOF motion control of the tip of the device. This design approach for steering of devices causes several practical challenges: redesign and development of all types of guidewires and catheters is required (i.e., off-the-shelf guidewires or catheters can not be used); manufacturing costs may increase; and the limitations in accurately tracking and visualizing the tip continue to exist (depending on type of imaging modality used in guidance).

Another attempt at addressing these problems is to utilize a secondary device with an expandable distal end that is covered by a sheath. In this design, the extraction and retraction of the distal end from the sheath results in expansion or contraction of the distal end. Further, the distal end has multiple channels for passing one or multiple guidewires that are placed at fixed relative positions with respect to each other. With this design, the user can change the channel for the guidewire to reach a different discrete location. While this design accommodates any off-the-shelf guidewire, it only provides very limited discrete position adjustment of the tip and does not address the limitations in visualization and image guidance.

The limitations in control, visualization and navigation of devices, create challenges for various procedures. For example, in cardiac ablation, it is desired to accurately and reliably control the tip of an ablation catheter to deliver energy to specific targets, with the purposes of restoring normal cardiac rhythm. For this purpose, the tip of an ablation catheter must be maintained at a suitable angle with the myocardium at a specific location, and with a safe but minimum force level during the ablation process. However, the limitations in catheter navigation create challenges in performing this task reliably, and in a repeatable fashion and ultimately leads to high failure rates and adverse events.

As another example, an interatrial transseptal puncture is needed to gain access to the left side of the heart from the right side for several procedures. For the transseptal puncture, typically a hollow catheter (e.g. steerable sheath) is used to guide the needle tip to the target site for puncture. Due to the limitations in visualization of the needle with respect to the anatomy and the challenges in reliably orienting and positioning the device, several major complications may arise: cardiac tamponade, aortic root puncture, embolic stroke, transient ST elevation of inferior leads and iatrogenic atrial septal defect.

Another example for cardiac procedures, is resynchronization therapy through the implantation of cardiac pacemakers. Such procedures generally involve implanting the tip of the pacemaker leads at various targets as required. However, the leads are at the tip of catheters that suffer from the previously mentioned limitations and therefore, it is difficult to reliably and accurately position them at the desired target and screw/mount the leads on the myocardial wall.

In yet another example, in an endovascular approach for the treatment of an abdominal aortic aneurysm, endovascular aneurysm repair (EVAR), an expandable stent graft is placed minimally invasively within the aorta. In such procedures, it is important to connect the main stent to other supplying arteries through several other stent grafts. However, as an initial step, typically a guidewire is used to direct the placement of the stent grafts, a process generally referred to as gate cannulation. Depending on the position, and orientation of the point of connection of interest, gate cannulation may take a long time, as the guidewire is being maneuvered in a large cavity (i.e. within the arteries or aneurysm), is under pulsatile blood flow, and may not have mechanical resting points to facilitate steering and navigation. As a result, such procedures can take an excessively long time and have considerable failure rates.

In yet another example, in a transaortic valve implantation, a guidewire may be used to facilitate positioning and alignment of the valve for implantation. However, navigating the guidewire through the valve as an initial step may be a challenging procedure as the guidewire is flexible, operating in a large space, and experiencing large pulsatile blood flow, while the procedure is generally guided with 2D projection x-ray or ultrasound. As a result such procedures can take an excessively long time and may have high failure rates or suboptimal outcomes.

In another example, for the treatment of atherosclerosis, in an endovascular approach, an initial step involves passing a guidewire through the occlusion, which then facilitates placing the balloon and/or stent. However, the guidewire tends to stay on the periphery of the arterial wall, and experiences buckling when under pressure. These limitations, together with the limitations in 2D projection x-ray fluoroscopy that is typically used to guide such procedures, leads to high technical failure rates and limitations in effectively crossing the occlusion.

Imaging of the interior of the body has applications for: assessment of function, tissue structure, anatomy, and composition for diagnostic purposes; planning and/or guiding interventions on target regions of the body; and assessing and monitoring the effect of the interventions on the target region. Example applications of internal imaging include imaging of various regions of the anatomy, including the gastrointestinal system, lungs, the cardiovascular system (including coronary, peripheral and neurological vasculature), the genitourinary systems, breast tissue, liver tissue and many others. As a specific example, imaging of the cardiovascular system with high frequency ultrasound or optical coherence tomography has been developed for assessing the structure and composition of arterial plaque.

Existing minimally invasive imaging probes face several limitations: the relative position of the imaging device relative to the anatomy may be uncertain or unknown, which hinders the creation of large fields of view or reconstruction of larger navigational maps and limits the usefulness of the obtained information due to the uncertainty in the location of the target; most interventional imaging probes, particularly based on ultrasound technology, are "side-looking" and forward looking devices generally have limited fields of view, or limited resolution, as little space is available to fit the required hardware at the tip of the imaging probe. Also, visualization of other therapeutic or interventional devices relative to the obtained images can be difficult and variable in many imaging modalities, such as ultrasound imaging, which may limit the application of such imaging equipment for guiding such procedures. Furthermore, 3-dimensional volumetric imaging is difficult to achieve through integration of large multi-dimensional sensor or transceiver arrays due to the limited available space within a minimally invasive probe.

Various properties of tissue can be measured by means of different technologies for imaging and for guidance of interventional procedures. For example, the acoustic impedance of tissue may be measured and detected with ultrasound transducers. Such information may also be used for detecting the shape of the anatomy of interest as well. The elastic properties and stiffness of soft tissue can also be characterized with ultrasound-based technology. An alternative method to elastography is direct force measurements through direct application of a known mechanical excitement input to the desired target surface and by monitoring the interaction forces and tissue response.

Another imaging modality that may be integrated in an imaging probe is optical based technology. Examples include: Ramon spectroscopy, fluorescence spectroscopy, near infrared spectroscopy, or optical coherence tomography (OCT). Such imaging techniques may utilize fiber optic-based solutions for the delivery or sensing of light. Alternatively, similar methods can be used to deliver laser-based ablation and photodynamic therapy.

Another imaging modality that may be integrated in an imaging probe is electric based technology which may be used to measure the electric conductivity, permittivity and impedance of tissue which may be measured using surface electrodes, or by measuring the reflected responses of tissue to incoming electromagnetic wave signals with known characteristics.

Another imaging modality that may be integrated in an imaging probe is a nuclear activity detector which may be utilized to measure high energy radiation because of nuclear activity at various locations of tissue, which may be possibly because of accumulation of a radioactive contrast agents at the target site of interest.

Regardless of the technology that is used, creating a forward looking and minimally invasive imaging device, capable of creating 2-dimensional or 3-dimensional images, with large field of views and high spatial resolution, and from specific target locations is difficult due to the challenges of integrating and embedding the hardware within the probe as well as limitations in tracking the probe relative to the anatomical structure of interest. A solution to address these limitations is desired.

Furthermore, a method that allows for tracking and positioning a therapeutic or diagnostic device (e.g. catheter) relative to the obtained images in order facilitate minimally invasive image guided interventions is desired as the visualization of other interventional devices can be challenging in many imaging modalities. For example, ultrasound may be subject to artifacts that may hinder its use in image guidance. Such artifacts may lead to the variable visibility of devices in the field of view depending on their alignment with respect to the ultrasound beams used for imaging. For example, the reflectivity of the materials of the devices being imaged and the device's surface texture can affect its visibility on the acquired images. Similar limitations impede the utility of many imaging modalities for minimally invasive image guided interventions. A solution to address these limitations is desired.

Accordingly, devices, systems, and methods which address these limitations in steering, tracking, and navigation during interventional procedures are desired.

SUMMARY

Embodiments disclosed address the limitations in reliable and accurate navigation of interventional devices for cardiovascular procedures. Embodiments disclosed relate to systems and methods that allow for accurate maneuvering and positioning of the catheter and tracking and visualizing its position relative to the anatomy. The proposed systems and methods incorporate a steering mechanism that comprises an expandable structure that can be controlled to spread out within an anatomical site of interest (e.g. vessel, cardiac chamber, stent graft, or anatomically relevant cavity) and may apply circumferential force to the tissue upon expansion. Once this structure is expanded, it provides several mechanical pivot points, or resting points, for a corresponding number of strings or strings that are connected to a flexible catheter positioned inside the expanding structure. In an embodiment the strings are connected to the eyelet or opening of the internal catheter from one end while the other end of the strings extends along the length of the device up to the handle. The internal catheter is configured to allow for passing of interventional devices, such as therapeutic catheters or guidewires, through it. Also, the internal catheter may be configured to allow the integration of an energy source and/or sensor. By manipulation of the strings from the handle end, the eyelet of the internal catheter can be manipulated with two DOF that allow controlling its position, and therefore the position of a device that is inside the internal catheter.

In embodiments, a set of position sensors measure the position or relative motion of the strings. For example, encoders may be mechanically coupled to the strings. The position sensors are configured to measure and track the position of the internal catheter relative to the expanding structure, by measuring the translation of all strings connected to it.

Also, in an embodiment, the position of a therapeutic device within the internal catheter may be measured with a motion sensor.

Embodiments disclosed herein address the limitations in steering of conventional interventional devices such as guidewires, catheters, and needles. Embodiments relate to systems and methods that allow for accurate maneuvering of the guidewire tip and facilitates effective steering of any off-the-shelf guidewire, catheter, or needle. The proposed systems and methods incorporate a steering mechanism that comprises a set of expandable structure, such as expandable branches, that can be controlled to spread out within the vessel lumen, or cardiac chamber, and apply circumferential force to the tissue. The structure or branches, once spread out, act as anchor points for a set of strings that support an eyelet within the assembly and vessel. The eyelet is configured to allow the guidewire or catheter to pass through it. Using strings, the eyelet can be manipulated with two DOF that allow controlling the position of a guidewire, or catheter tip in a plane perpendicular to the vessel, or cardiac chamber, (or otherwise in a geometrically-defined area, or surface shape relative to the vessel or cardiac chamber) at the location of expansion of branches.

In embodiments, a set of encoders are mechanically coupled to the strings. The encoders are configured to track the position of the eyelet and guidewire or catheter. Using the tracking information, a user interface depicts to the user the tip location by overlaying the tracked eyelet position on top of a navigation map of the mechanism workspace.

Embodiments disclosed address some of the limitations in existing minimally invasive imaging probes and current methods for minimally invasive image guided interventions. More specifically, the embodiments relate to systems and methods that allow for accurate positioning and tracking the position of an energy source and/or sensor relative to the anatomy as well as positioning and tracking a therapeutic or diagnostic device. The positioning and tracking of an energy source and/or sensor permit for reconstruction of volumetric imaging maps of the desired target anatomy.

In an embodiment, a source of energy and/or a sensor is integrated within the internal flexible catheter. The sensor, possibly in combination with the energy source, may be used to obtain measurements from the area surrounding the sensor or that in front of it. Such a method may be used to obtain images of the tissue at the desired anatomical site. As the position of the internal catheter and therefore the sensor can be controlled and measured, one can acquire measurements across the entire workspace of the mechanism by arbitrary positioning of the internal catheter at different locations within the expanding structure as its relative position is being tracked. As the measurements are made at different known positions the obtained information can be utilized to create large images of the tissue of interest and can be used to create navigation maps for guiding the procedure of interest.

Using the tracking information, comprising the position of the internal catheter and/or the travel of the device within the internal catheter, the relative position of the internal catheter or the therapeutic device can be estimated relative to the expanding structure and can be visualized for the user using a graphical user interface. The location of the eyelet of the internal catheter, or the position of the tip of the device within the internal catheter may be overlaid on top of a navigation map of the mechanism's workspace. The navigation map may also include the information obtained with the sensor integrated within the internal catheter. This allows the user to see the relative location of the device with respect to the medical images obtained and would enable them to see the device's position updated in real-time relative to the images as it is being manipulated.

In an embodiment, the user interface would also show a virtual representation of the interventional device relative to the anchoring expanded structure and would demonstrate to the user where the interventional device is based on the length that has exited the inner tube eyelet and based on the measured internal catheter position.

An embodiment includes a steering device for positioning an interventional device within a vessel lumen or cardiac chamber of a patient. The steering device includes a set of expandable structures, a set of strings, and an eyelet. The set of expandable structures can be controlled to spread out within the vessel lumen or cardiac chamber and apply circumferential forces to surrounding tissue. The set of strings use the set of expandable structures as anchor points. The eyelet has a ring-shaped perimeter and a central opening. The eyelet is surrounded by the set of expandable structures and is supported by distal ends of the set of strings which are secured around the ring-shaped perimeter of the eyelet. The eyelet is configured to permit the interventional device to pass through the central opening. Further, by using the set of strings, the eyelet can be manipulated with two degrees of freedom and permit control of the position of the interventional device in a geometrically-defined area relative to the vessel lumen or cardiac chamber at a location of the expandable structures.

An embodiment includes a steering device for positioning an interventional device within a vessel lumen or cardiac chamber of a patient. The steering device includes an internal catheter, a handle, an elongate sheath, a set of expandable branches, a set of strings, and an eyelet. The internal catheter is of flexible, elongate structure having a central lumen extending between a proximal end and a distal end. The handle is for user manipulation and steering control coupled to the proximal end of the internal catheter. The elongate sheath at least partially surrounds the internal catheter along its length. The set of expandable branches is located at the distal end of the internal catheter that can be controlled to spread out within the body vessel or cavity and applies circumferential forces to surrounding tissue by manipulating the set of expandable branches and the elongate sheath with respect to each other. The set of strings is coupled to the handle at proximal ends for user manipulation via the handle, extends within the elongate sheath along the internal catheter, and engages anchor points of the set of expandable branches prior to distal ends thereof. The eyelet has a ring-shaped perimeter defining a central opening. The eyelet is surrounded by the set of expandable branches and supported by the distal ends of the set of strings which are secured around the ring-shaped perimeter of the eyelet. The eyelet is coupled and aligned with the distal end of the internal catheter to permit the interventional device extending through the internal catheter to pass through the central opening of the eyelet.

An embodiment includes a steering device for positioning an interventional device within a vessel lumen or cardiac chamber of a patient. The steering device includes an elongate device assembly defining a central lumen extending therethrough. The assembly has a handle at a proximal end and an expandable structure at a distal end. The expandable structure includes a set of expandable branches, a set of strings, and an eyelet. The set of expandable branches can be controlled to spread out within the vessel lumen or cardiac chamber and apply circumferential force to surrounding tissue. The set of strings use the set of expandable branches as anchor points. The eyelet is proximate the distal end of the elongate device assembly, is supported by the set of strings and is sized to permit passage of an interventional device through it. Further, by using the set of strings, the eyelet can be manipulated with two degrees of freedom and permit control of the position of a tip of the interventional device in a geometrically-defined area based on the location of the expandable branches.

An embodiment includes a method for imaging and procedure guidance via an interventional device within a vessel lumen or cardiac chamber of a patient. The method includes providing an electromechanical steering device system that guides the interventional device. The electromechanical steering device system includes: a catheter with expandable branches and a eyelet at its distal tip that is controlled by a set of strings actuated by a handle; a plurality of position sensors mechanically coupled to the set of strings; a plurality of sensors mechanically coupled to at least one of the interventional device and the catheter; and a computing device communicatively coupled with the plurality of sensors, including: at least one processor and memory operably coupled to the at least one processor and configured to store instructions invoked by the at least one processor and a positioning and tracking engine configured for rendering and visualizing images; and a GUI display communicatively coupled with the computing device. The method includes moving a tip of the interventional device to a desired position(s) by actuating the handle and tracking the position of the interventional device. The method includes acquiring measurements from the plurality of sensors at the desired position(s). The method includes reconstructing a map of the vessel lumen or cardiac chamber of interest based on the acquired measurements. The method includes rendering and loading a virtual rendered device image. The method includes measuring the catheter position from the plurality of sensors. The method includes measuring the axial insertion of the interventional device within the catheter from the plurality of sensors. The method includes overlaying the virtual rendered device image on the map based on the measurements in an overlaid image presented on the GUI display.

An embodiment includes a method of obtaining images of tissue at a desired anatomical site using a steering device with an expandable structure at its distal end for guidance of an interventional device. The method includes: providing a sensor integrated within an internal catheter of the steering device; obtaining measurements from an area surrounding the sensor; controlling a position of the internal catheter and the sensor; acquiring measurements across an entire workspace by arbitrary positioning of the internal catheter at different locations within the expandable structure as its relative position is being tracked; utilizing the measurements to create large images of tissue of interest and navigation maps for guiding a procedure; and using the positions of the internal catheter and the travel of the interventional device within the internal catheter, for estimation of the relative position of the internal catheter to the expanding structure and producing a visualization on a graphical user interface.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which:

FIG. 5A is an end view of a handle of the steering device of FIG. 4, according to embodiments.

FIG. 7 is a view of an alternate handle of the device, according to an alternative embodiment

FIG. 10 is a view of the internal mechanism for actuation of the strings and tensioning them, according to embodiments.

FIGS. 16A-C demonstrate the concept of using the steering mechanism for acquiring measurements at multiple known positions in order to obtain an image of the anatomy of interest, according to an embodiment.

FIG. 19A demonstrates a potential approach and deployment of the device within a main stent graft for guidewire navigation in EVAR, according to an embodiment.

Figure 1:
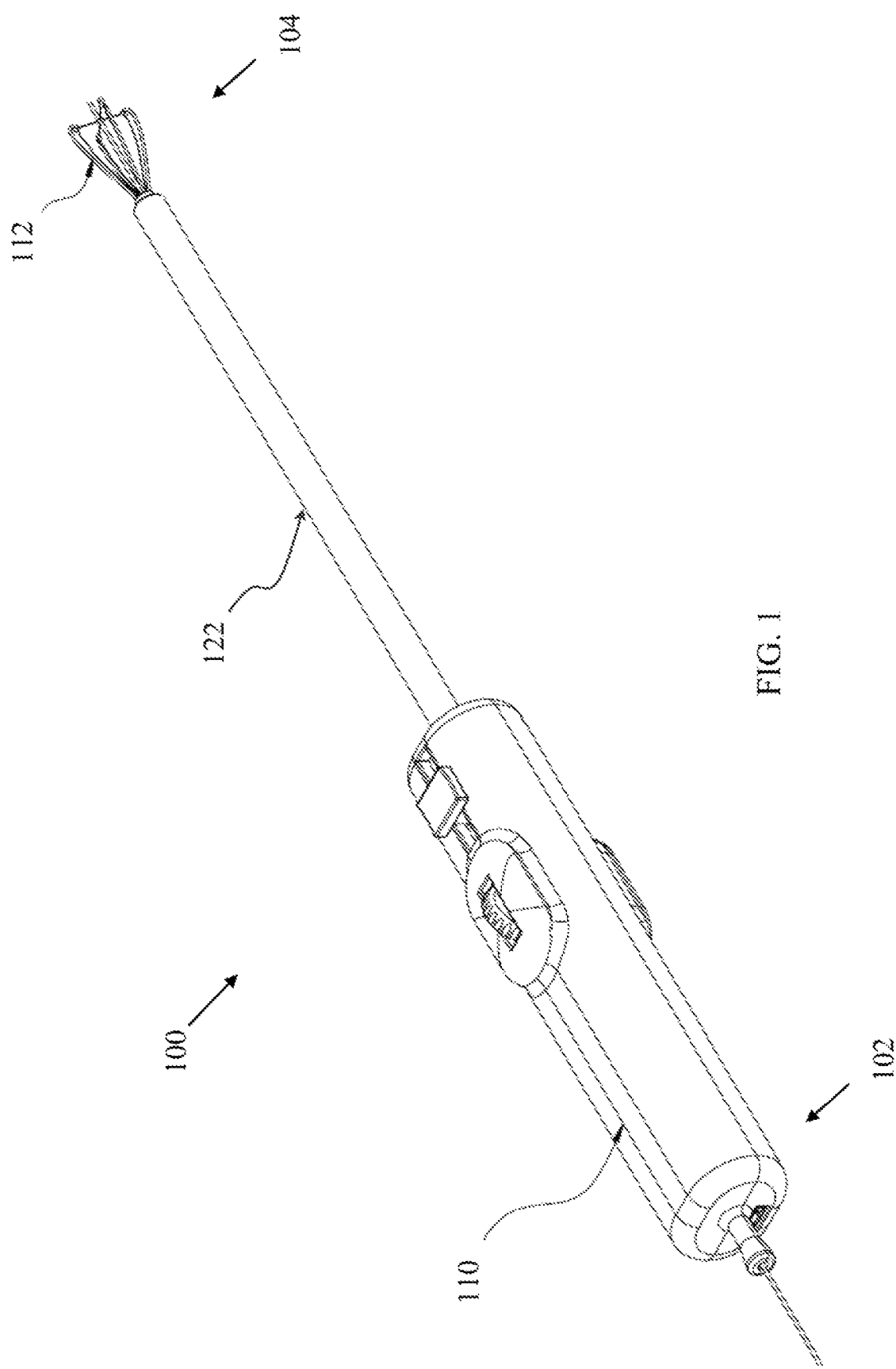
FIG. 1 is an isometric view of a steering device, in the form of a steerable catheter and imaging probe, according to embodiments.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

Disclosed herein are devices, systems and methods for steering conventional guidewires or catheters during endovascular interventions and catheterizations. The proposed system can comprise an electromechanical steering device and a software graphical user interface (GUI) running on a computer. Further disclosed herein are devices, systems and methods directed to a minimally invasive medical imaging probe that also allows for positioning and tracking of an interventional device relative to the anatomy and reconstructed images. The proposed system can comprise an electromechanical steering device with an integrated transducer and sensor, and a software for rendering and visualizing the images as well as a GUI running on a computer for diagnosis, procedure planning, and navigation guidance. Further, disclosed herein are devices, systems and methods for steering and navigation of devices for cardiovascular interventions. The proposed system can comprise an electromechanical steering device, and a software for a GUI running on a computer for diagnosis, procedure planning, and navigation guidance.

FIG. 1 depicts a steering device 100 according to an embodiment. Steering device 100 may alternatively or additionally be referred to as an imaging probe. Further, steering device 100 may additionally be referred to as a steering mechanism at times in this disclosure.

In one embodiment, steering device 100 includes a handle 110 at proximal end 102, a sheath 122 at least partially covering an internal catheter 130, and an expandable structure 112 at a distal end 104. In embodiments, handle 110 is configured to be held by the operator at proximal end 102 and further act as the controller portion of steering device 100 and/or steerable imaging probe. The expandable structure 112 at the distal end 104 is configured to enter a lumen of a body and is configured to be controlled by the operator via handle 110.

Figure 2:
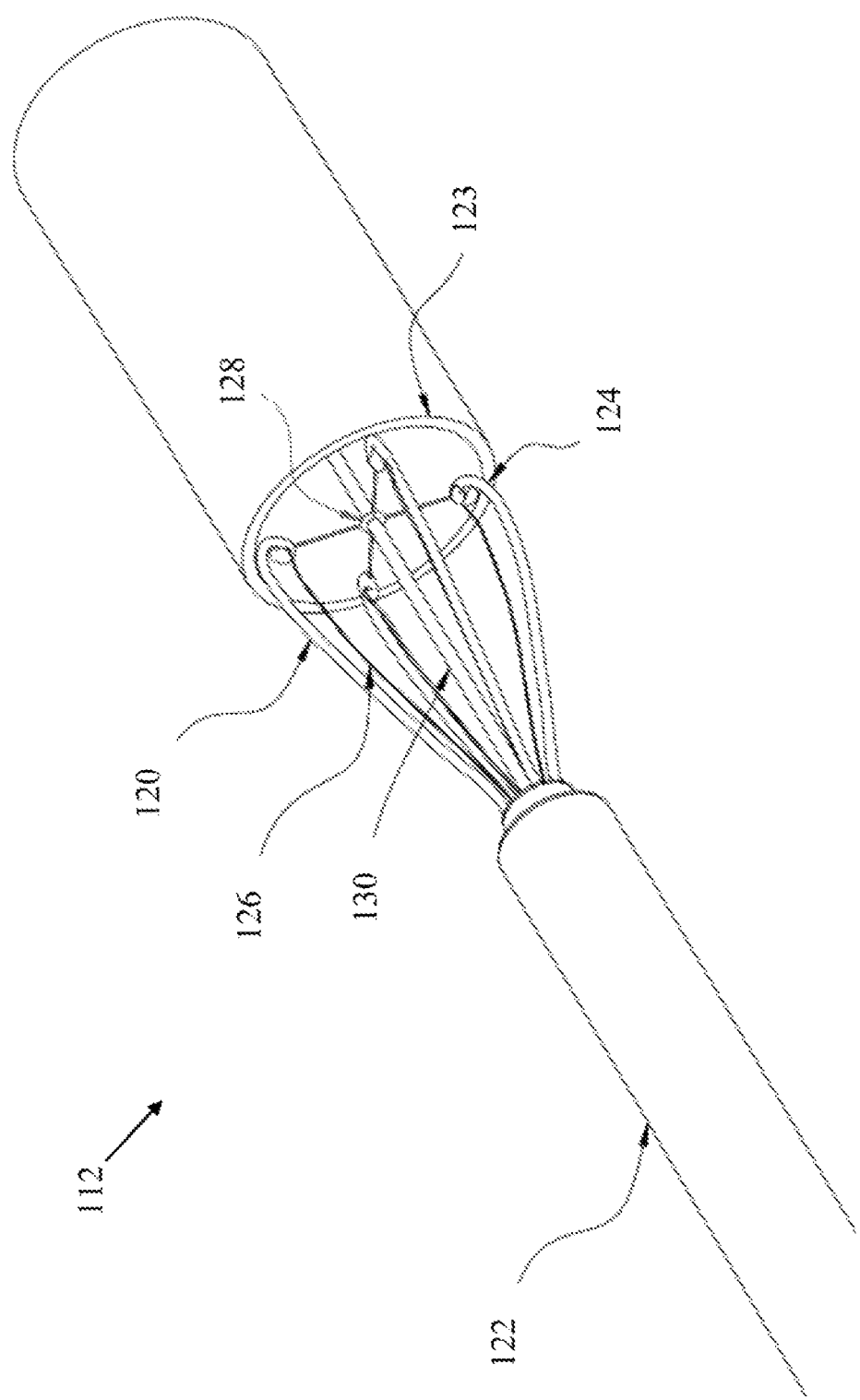
FIG. 2 is a close-up view of a distal end of steering device, according to embodiments.
Figure 3:
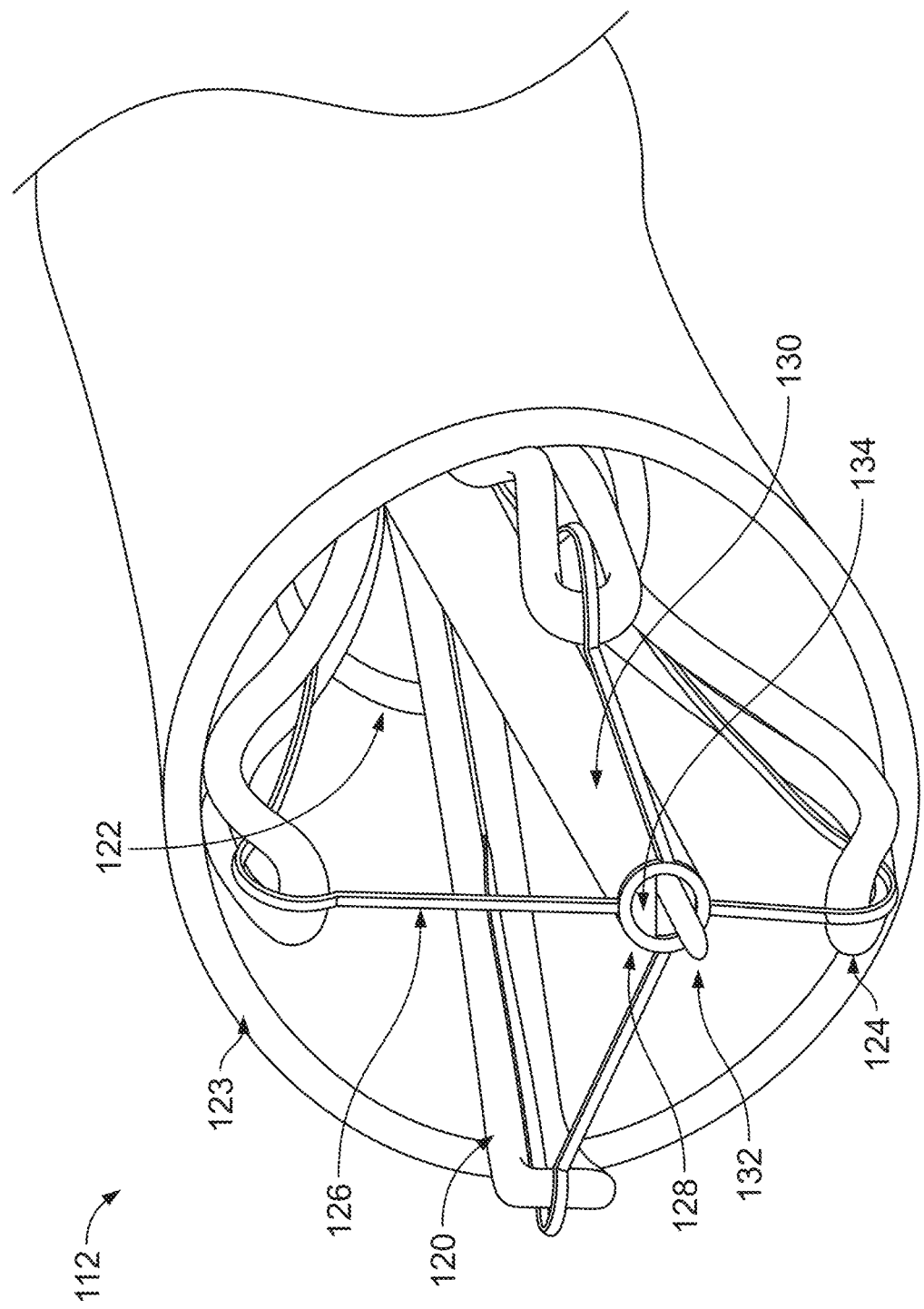
FIG. 3 is a view of the distal end of the device demonstrating the expandable support structure, according to embodiments.

FIGS. 2 and 3 show close-up views of the expandable structure 112 and distal end 104 of steering device 100, according to an embodiment. In one embodiment, expandable structure 112 consists of a set or a plurality of expandable branches 120 (also alternatively referred to as expansible branches 120). Branches 120 are mechanically biased to apply circumferential force and expand to a certain diameter. In an initial condition, branches 120 are mechanically constrained within a sheath 122. When the branches 120 are extracted from the sheath 122 they expand within the vessel lumen and apply circumferential force towards a vessel wall (or cardiac chamber) 123 and may anchor and become relatively fixed with respect to the lumen, or chamber, once they have expanded (anchoring function). Once expanded, or fixated against a vessel wall or cardiac chamber, the tip of each one of these branches 120 acts as a mechanical leverage or anchor point 124.

Although devices with a set of expandable branches as a type of expandable structure are primarily discussed in this disclosure, other sets of and forms of expandable structure are contemplated as well, including various expanding meshes, surfaces, components, projections or features. Further, anchor points 124 may be referred to as pivot points in this disclosure as well. These anchor points 124 each support a plurality of strings 126 that are connected to an eyelet 128 of an internal catheter 130. Throughout this disclosure, references to "strings" should be understood to broadly refer to any type of strings, pull-wires, or similar manipulable components made of metal, fabrics, polymers, or crystals. In an initial condition, without any force exerted on strings 126, eyelet 128 is concentric to sheath 122 and the vessel wall 123.

Eyelet 128 is generally a structure having a ring-shaped perimeter and a central opening. Eyelet is generally surrounded by the expandable branches 120 and is supported around its ring-shaped perimeter by the distal end of strings 126. Further, a guidewire or catheter 132, passes through the internal catheter 130 and therefore may extend through the central opening and out from the eyelet 128. It should be understood that guidewires 132 and catheters are examples of interventional devices that can be used with the steering devices 100 disclosed herein. Steering devices 100 can position such interventional devices within a vessel lumen or cardiac chamber of a patient, for example. The base of the branches 120 are connected to the internal catheter/tube 130 and they are all initially positioned within the sheath 122. It is the motion of internal catheter 130 relative to sheath 122 that results in the extraction of branches 120 from sheath 122 and their expansion, or retraction of branches 120 into sheath 122 and their compression. In an embodiment, there are transmitters and, or, receivers that serve as sensors 134 integrated within the internal catheter 130. The sensors 134 can be used to obtain measurements from the surrounding anatomy and particularly from the space in front of the sensor 134.

In the embodiment in FIG. 3, branches 120 of the expandable structure 112 at the distal end of the device are illustrated in an open and anchored position where they are pressing against the vessel wall 123. The guidewire 132 passes through the lumen of the internal catheter 130 and through the eyelet 128. Eyelet 128 is located in the center of the device and is steered by manipulation of strings 126.

Branches 120, as depicted in FIG. 3, may be constructed by deforming and welding a rod (e.g. stainless steel or nitinol) to the desired shape using laser welding techniques. In an embodiment, branches 120 may be welded to a metallic cylinder, and embedded at the tip of an internal tube as depicted in FIG. 3. Alternatively, branches 120 may be laser-cut from a tube of the desired material.

In general, by using the set of strings 126, the eyelet 128 can be manipulated with two degrees of freedom and permit control of the position of the interventional device in a geometrically-defined area relative to a vessel lumen or cardiac chamber at a location of the set of expandable structures. In some embodiments, the eyelet 128 may be positioned in a plane perpendicular to the vessel lumen or cardiac chamber at a location of the expandible branches 120. In some embodiments, the eyelet 128 may be positioned according to a surface shape or other geometry, such as a dome-shape.

Figure 4:
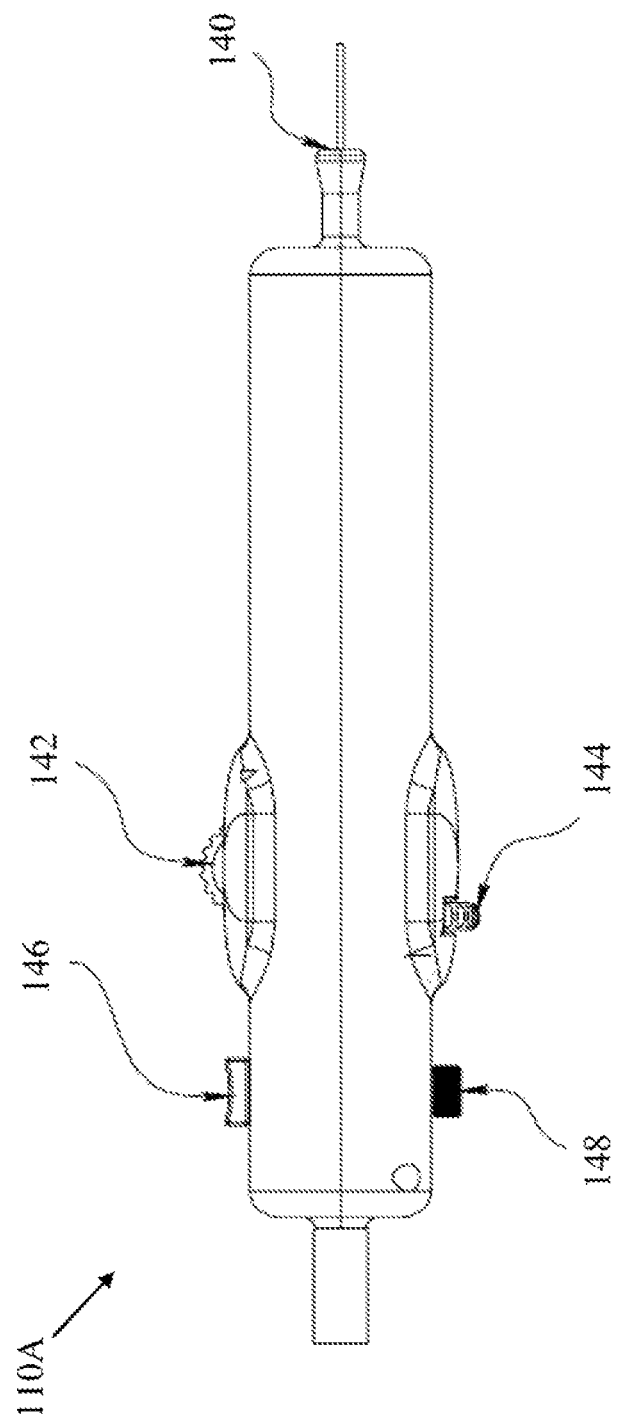
FIG. 4 is a close-up view of a handle of a steering device, according to embodiments.
Figure 5B:
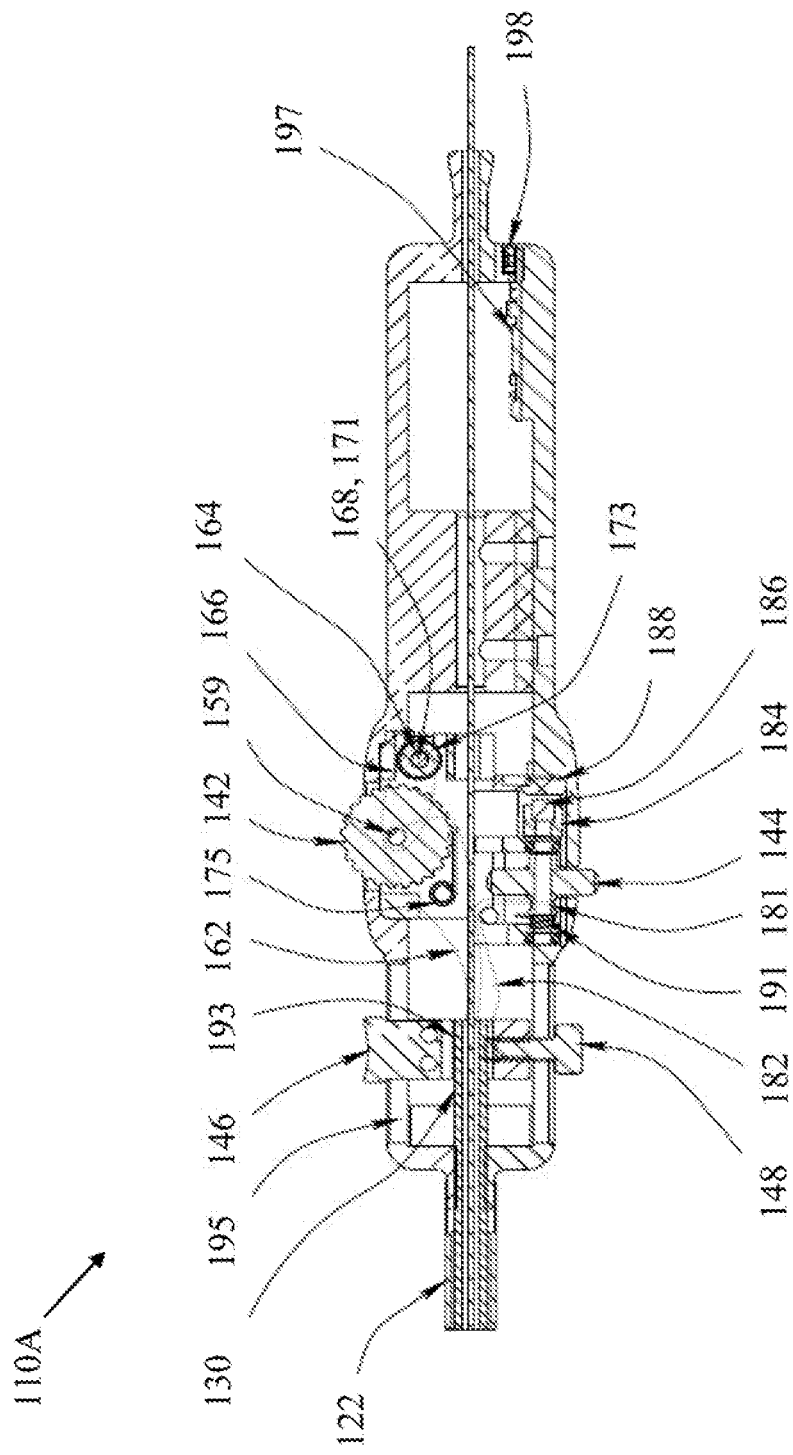
FIG. 5B is a cross-section view of a handle of a steering device of FIG. 5A, according to embodiments.
Figure 6:
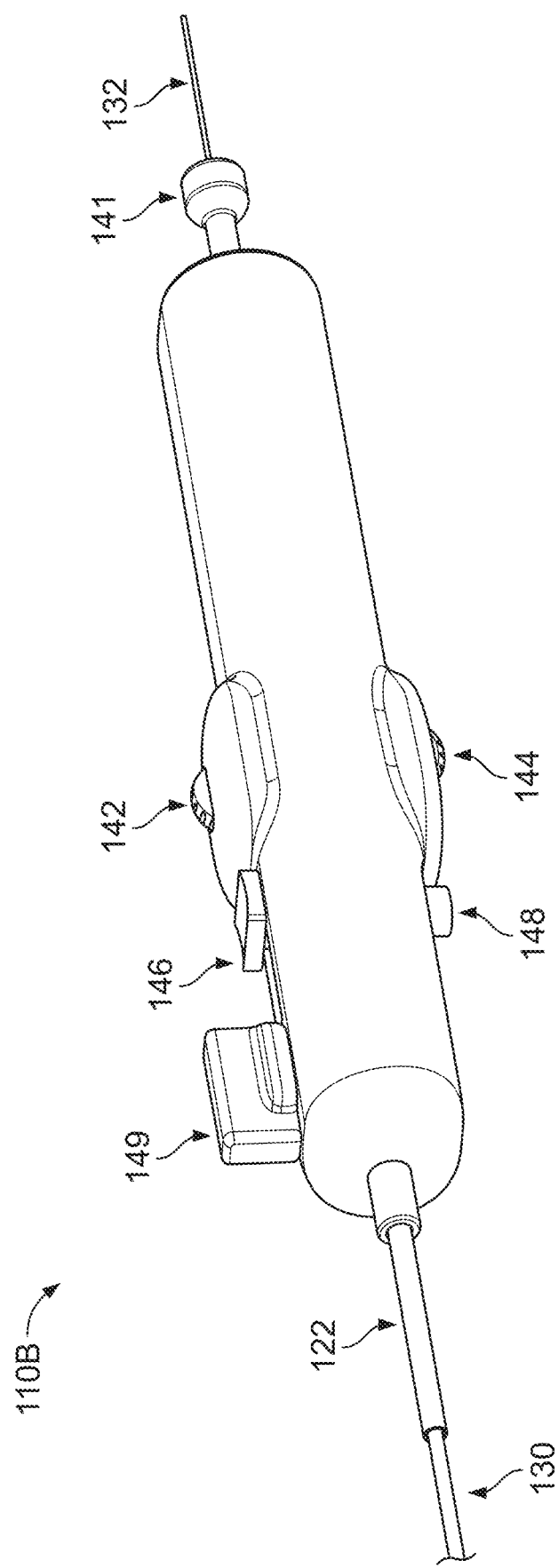
FIG. 6 is a view of an alternate handle of the device, according to embodiments.

FIGS. 4 to 5B disclose a first embodiment of a handle 110A and other components of a steering device 100. FIGS. 6 and 7 disclose additional alternate embodiments of similar handles 110B and 110C of a steering device 100. At times in this disclosure, any of these handles 110A, 110B and/or 110C may be generically referred to individually or collectively as a handle 110. Further, similar components in these handles 110 are referred to with the same reference numerals in some instances. FIGS. 8-12B provide depictions of generally internal mechanisms for use with one or more of these handles 110. The mechanisms should be viewed as being broadly contemplated and applicable to any of the handle arrangements or similar configurations to which they may apply or can be implemented.

FIG. 4 is a close-up view of handle 110A of steering device 100 according to an embodiment. In embodiments, handle 110A includes an opening 140 for the insertion of a catheter or guidewire 132. Handle 110A can include a top roller wheel 142 and a bottom roller wheel 144 that use a set of mechanisms to allow for steering of eyelet 128. Top roller wheel 142 can be rotated along an axis perpendicular to the main axis of handle 110A. Bottom roller wheel 144 rotates along an axis parallel to the main axis of the handle 110A. A slide 146 is coupled to the internal catheter 130 and allows for the extraction or insertion of branches 120. Slide 146 also has a locking mechanism achieved with a fastening screw 148 that allows locking of the position of internal catheter 130 relative to sheath 122. The locking feature allows for controlling the extraction amount of branches 120. In alternative embodiments, depending on the number of strings 126 that are manipulated, the number of rollers and corresponding mechanisms may vary.

FIG. 5A depicts an end view of handle 110A of the steering device 100. FIG. 5B depicts a cross-section view of handle 110A of steering device 100 viewed from section A-A of FIG. 5A. In the embodiment of FIG. 5A, top roller wheel 142 includes a boss 159 for coupling to a first string loop 162. Top roller wheel 142 is also mechanically coupled to an encoder shaft 164 through another coupling mechanism 166. Encoder shaft 164 is coupled to a magnet holder 168 that is configured to hold magnet 171 of magnetic encoder sensor 173 at a fixed distance from magnetic encoder sensor 173. A tensioning mechanism 175, which includes a spring, may be used to maintain tension on first string loop 162. In other embodiments of the mechanism coupling string 126 to top roller wheel 142, tensioning and sensing methods may vary.

In embodiments, bottom roller wheel 144 has an extension boss 181 for coupling to a second string loop 182. Bottom roller wheel 144 is also mechanically coupled to another encoder magnet holder 184. Magnet holder 184 is positioned to hold magnet 186 of a magnetic encoder sensor 188 at a fixed distance from magnetic encoder sensor 188. A tensioning mechanism 191, including a spring may be used to maintain tension on second string loop 182. In other embodiments of the mechanism coupling string 126 to bottom roller wheel 144, tensioning and sensing methods may vary.

In embodiments, slide 146 and tensioning screw 148 allow for extraction and withdrawal of internal catheter 130 within the sheath 122. Slide 146 is extended and has an opening 193 which couples to internal catheter 130. Slide 146 can travel along a slit opening 195 in the handle body.

In an embodiment, handle 110A also houses a circuit board 197, that contains all the necessary electronics and embedded systems to capture the position of the encoders and transmit that information to a host computer through a port 198 (e.g. USB) or wirelessly.

FIG. 6 is a close-up view of handle 110B of steering device 100 according to an embodiment. In embodiments, handle 110B comprises a sealing valve 141 for the insertion of a catheter or guidewire 132. Handle 110B can include a top roller wheel 142 and a bottom roller wheel 144 that use a set of mechanisms to allow for steering of eyelet 128 or internal catheter 130. Top roller wheel 142 can be rotated along an axis perpendicular to the main axis of handle 110B. Bottom roller wheel 144 rotates along an axis parallel to the main axis of the handle 110B. A slide 146 is coupled to the internal catheter 130 and allows for the extraction or retraction of branches 120. In an embodiment, slide 146 also has a locking mechanism achieved with a fastening screw 148 that allows locking of internal catheter 130 position relative to sheath 122. The locking feature allows for controlling the extraction range of the branches 120. A knob 149 allows for applying tension on strings connected to the tip of the outer sheath 122. With different indentation hardness along the length of the sheath, the tension on the strings, created by rotation of the knob, leads to deflection of the softer distal segment of the sheath. In alternative embodiments, depending on the number of strings 126 that are manipulated, the number of rollers and corresponding mechanisms may vary.

In an alternative embodiment, shown in FIG. 7, a handle 110C has a slide 146 for advancing the internal catheter 130 and allows for extraction or retraction of branches 120. Handle 110C further includes a steering mechanism 160.

Figure 8A:
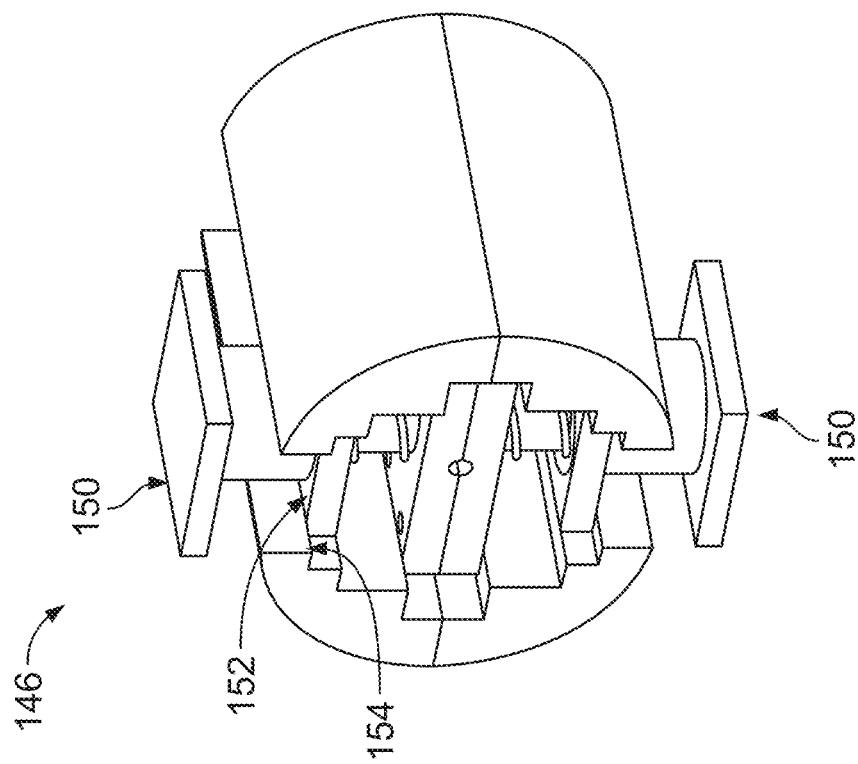
FIGS. 8A and 8B are views of a mechanism to deploy the expandable structure, according to an embodiment.
Figure 8B:
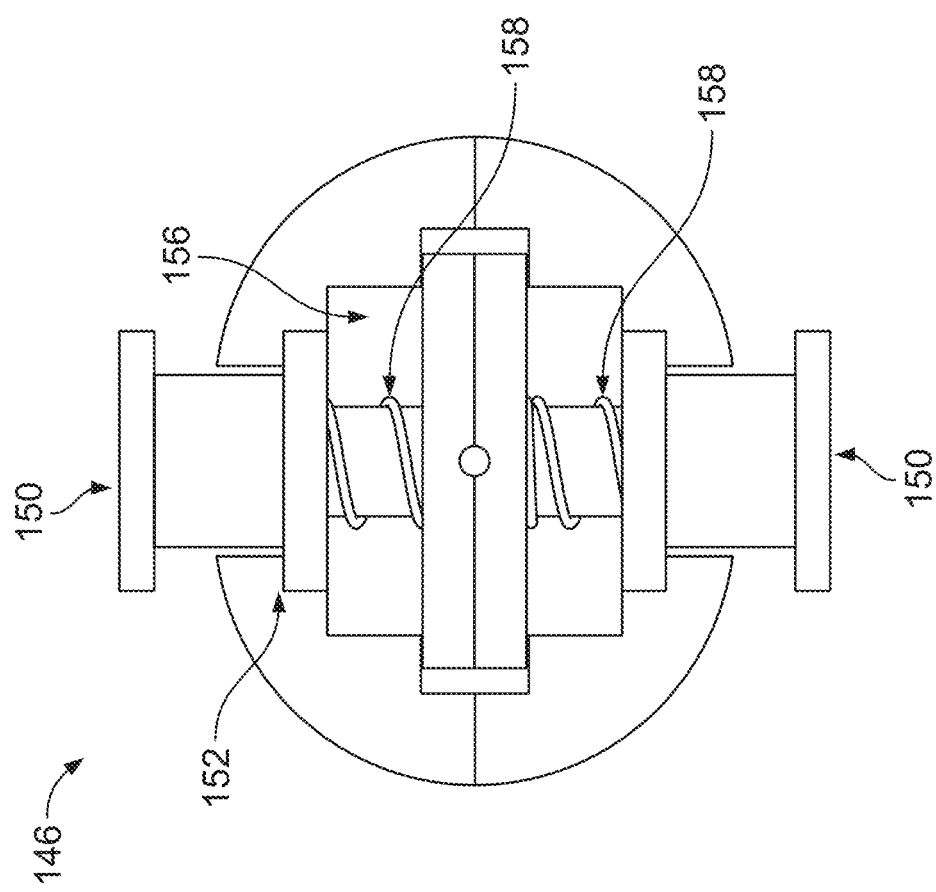

FIGS. 8A and 8B show the slide 146 from multiple perspectives. A slide 146 similar to this could be used with handle 110C or variations of the other handle 100 designs. This slide 146 allows for extracting or retracting of the internal catheter 130 and the branches 120 within the sheath 122. In an embodiment, the slide 146 of the handle 110, uses two opposing surfaces 150 that are gripped by the user. An extension 152 of the opposing surfaces 150 are pressed against a surface 154 by use of springs 158 inside the cavity 156 within the handle 110. The application of force from the springs 158, creates friction between two surfaces 152 and 154 and prevents the slide 146 from moving. The user can adjust the extraction of the internal catheter 130 by pushing on the opposing surfaces 150 to relieve the friction between the two surfaces 152 and 154 and allow moving the slide 146 and therefore extracting or retracting the internal catheter 130.

Figure 9A:
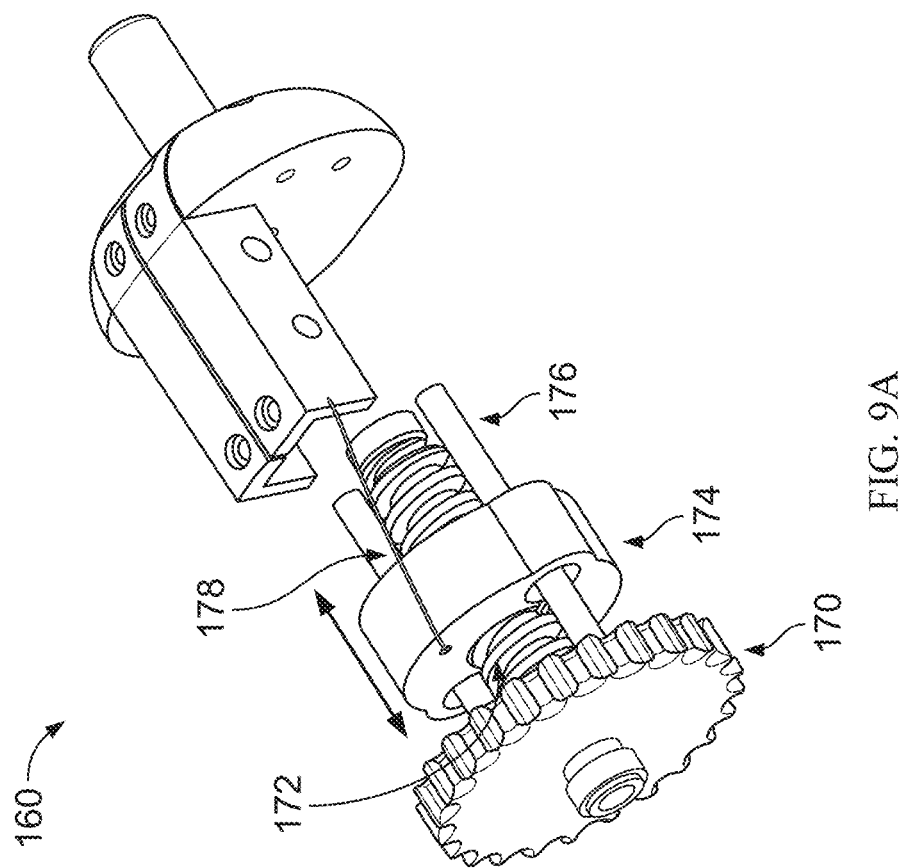
FIGS. 9A and 9B are views of a steering mechanism for deflecting the distal end of the outer sheath, according to embodiments.
Figure 9B:
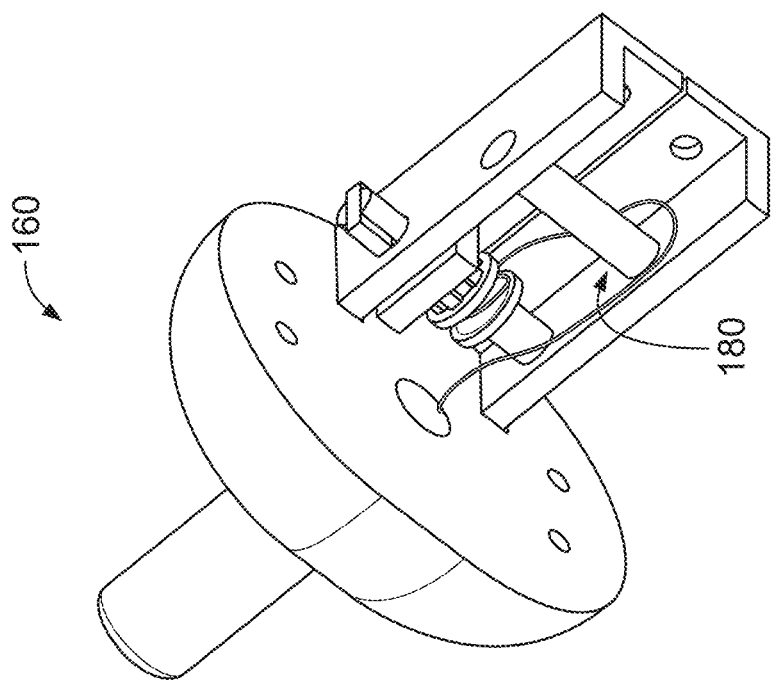

In one embodiment, the handle 110 utilizes a steering mechanism 160 to allow for deflecting the distal end of the outer sheath 122 as shown in FIG. 9A and FIG. 9B. A steering mechanism 160 similar to this could be used with handle 110C or variations of the other handle 100 designs. As is illustrated, the steering mechanism 160 utilizes a rotary dial 170 connected to a spiral gear 172. The spiral gear 172 engages with a nut 174 that is constrained with two guide rails 176 to travel axially as the nut 174 and spiral gear 172 engage. A string 178 which connects to one end of the distal end of the sheath 122 is connected to the nut 174. Travel of the nut 175 allows for creating tension on the string 178 and allows for deflecting the distal end of the sheath 122. In an embodiment, the sheath 122 may have two strings on opposite sides of the sheath 122 to allow for bi-directional steering.

In an embodiment, the second string 180 may be connected as illustrated in FIG. 9B and initially during assembly of the catheter handle 110 the second string 180 can be tensioned such that the distal end of the sheath 122 is biased in the direction of the corresponding guidewire. This permits bi-directional steering by relaxing or applying tension on the first string 178 through actuation of the rotary dial 170 and the travel of nut 174.

FIG. 10 demonstrates an embodiment of the internal mechanism within a handle 110 that can be used for pulling on the strings 126 and sensing their position. Typically, two sets of such a mechanism would be inside the device handle 110 and would allow the user to manipulate the internal catheter 130 and the eyelet 128 with two degrees of freedom. In the embodiment depicted in FIG. 10, the free ends of strings 126 are connected to gears 192 and during assembly, the gears 192 can be rotated to allow for tensioning of the strings 126 to a desired level. A spring or other tensioning mechanism could also be used to apply further tension on the strings 126. The central gear 194 is mechanically coupled to the wheels 142 or 144 to be manipulated by the user. The gear 196 is coupled to the previous gears and is connected to a position sensor such as an encoder wheel to permit sensing the actuation of the strings 126. This design facilitates the assembly of the device and allows for the assembler to tension the strings 126 as desired before placing the other gears 194 and 196 which would fixate the relative position of gears 192 and maintain the set tension on strings 126.

Figure 11A:
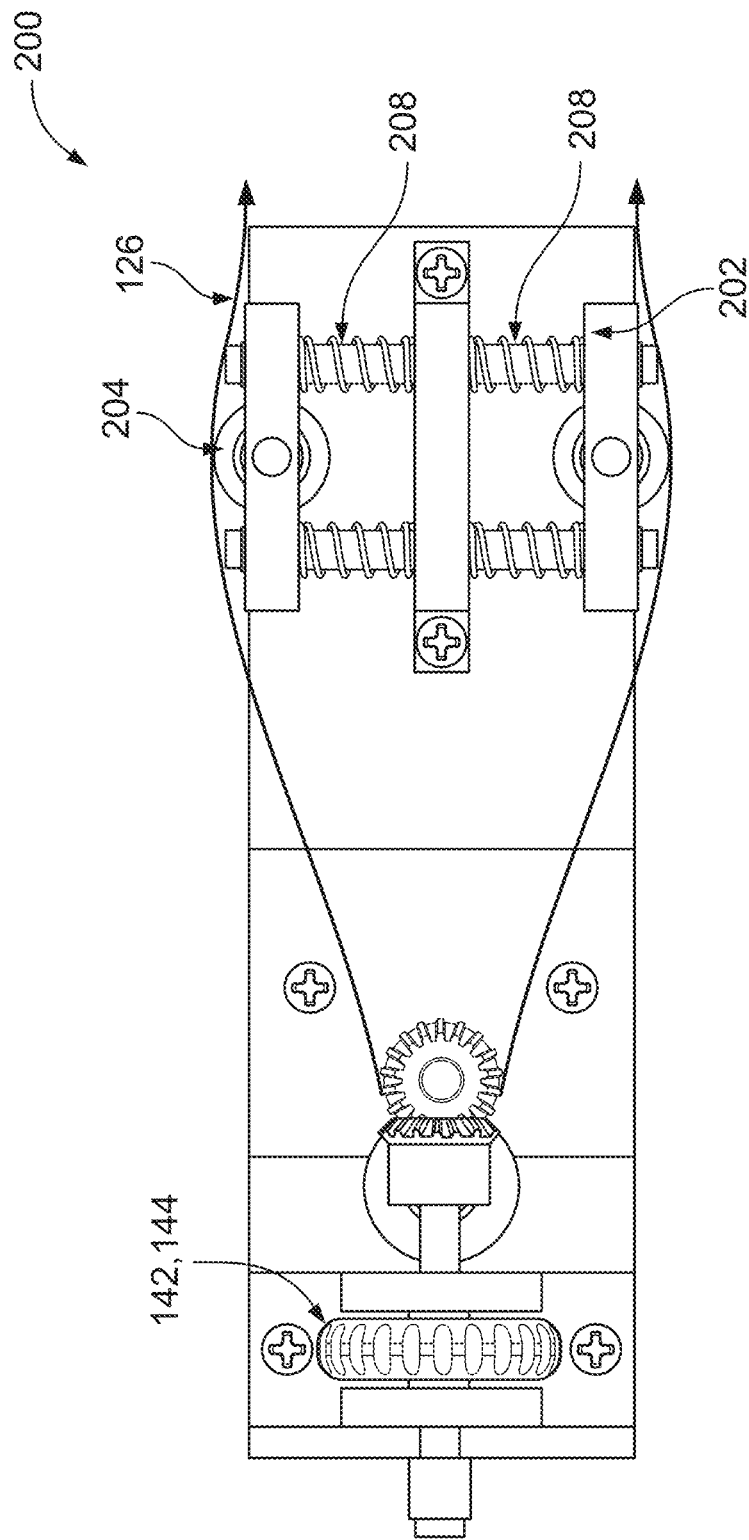
FIG. 11A is a top side view of the internal mechanism for actuation and tensioning of the strings, according to an alternative embodiment.
Figure 11B:
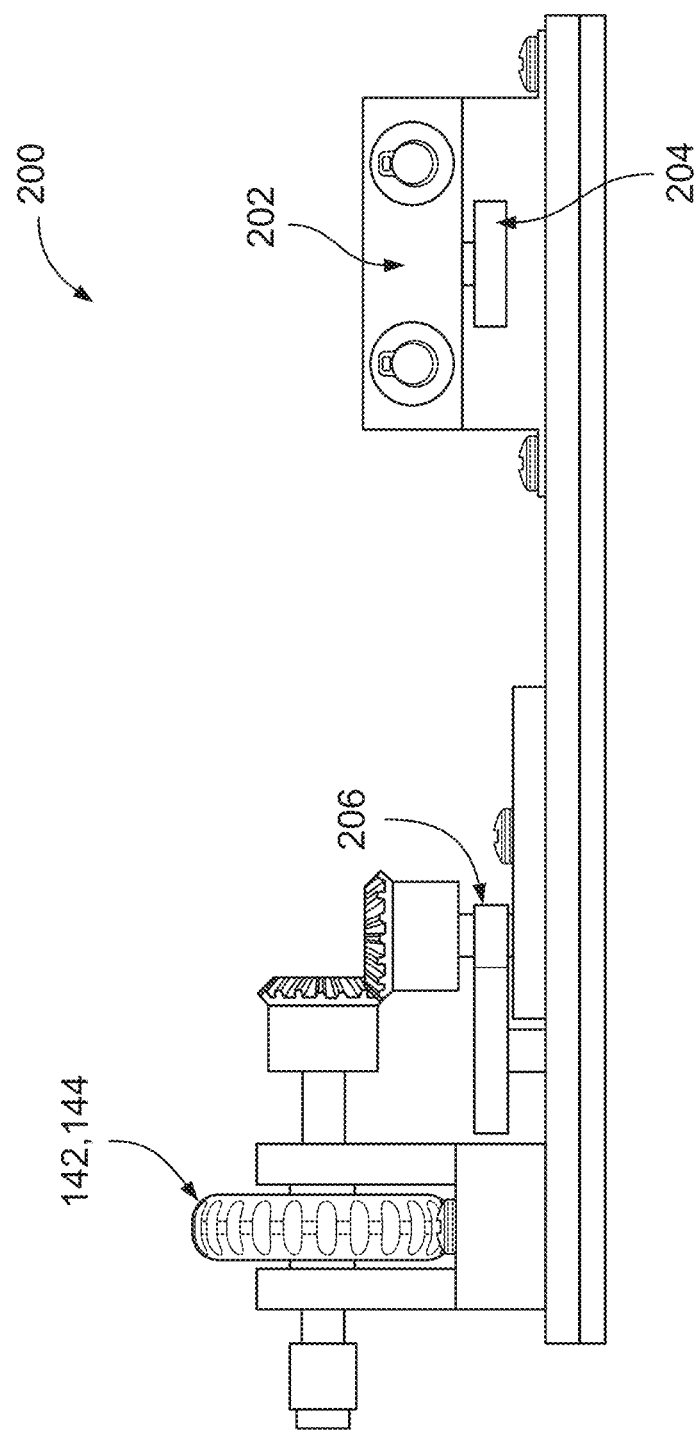
FIG. 11B is a side view of the internal mechanism for actuation and tensioning of the strings, according to an alternative embodiment.
Figure 11C:
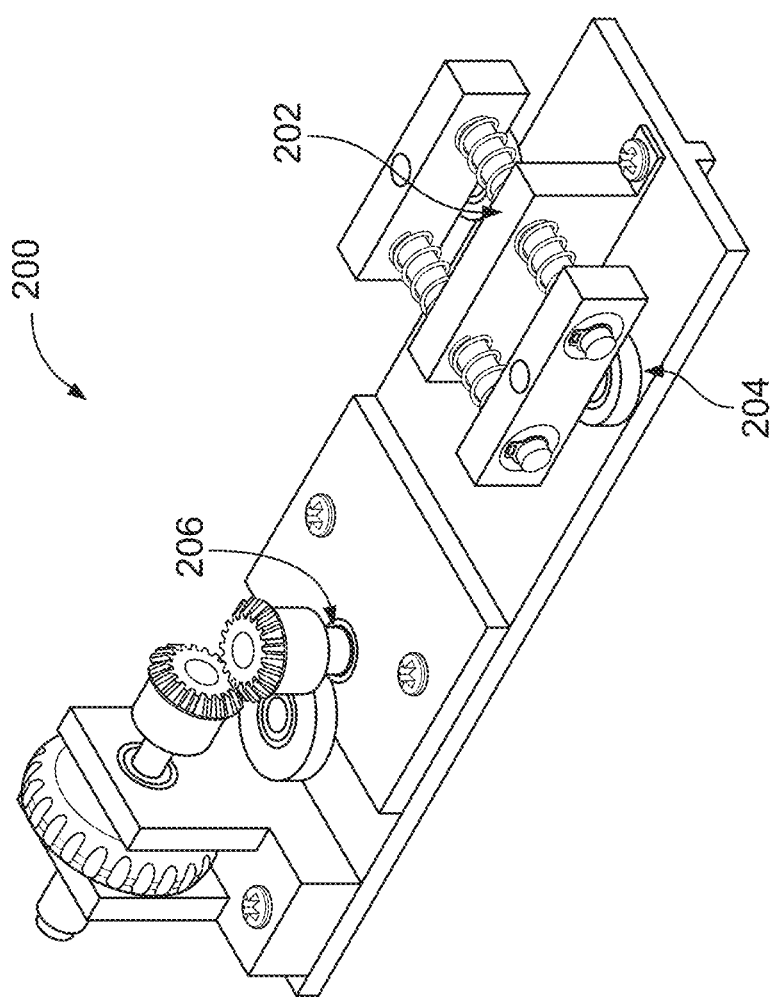
FIG. 11C is an isometric view of the internal mechanism for actuation and tensioning of the strings, according to an alternative embodiment

FIGS. 11A-C show an alternative embodiment of the internal mechanism 200 for manipulation of the strings 126 and sensing their position. This embodiment utilizes a spring mechanism 202 to tension the strings 126 as desired during the assembly process. The strings 126 are coupled to the tensioning mechanism 202 through roller wheels 204. The roller wheels 204 are pushed outward for tensioning by an array of springs 208. The strings 126 are also connected to a main roller 206 that is mechanically coupled to the roller wheel 142 or 144 actuated by the user.

Figure 12A:
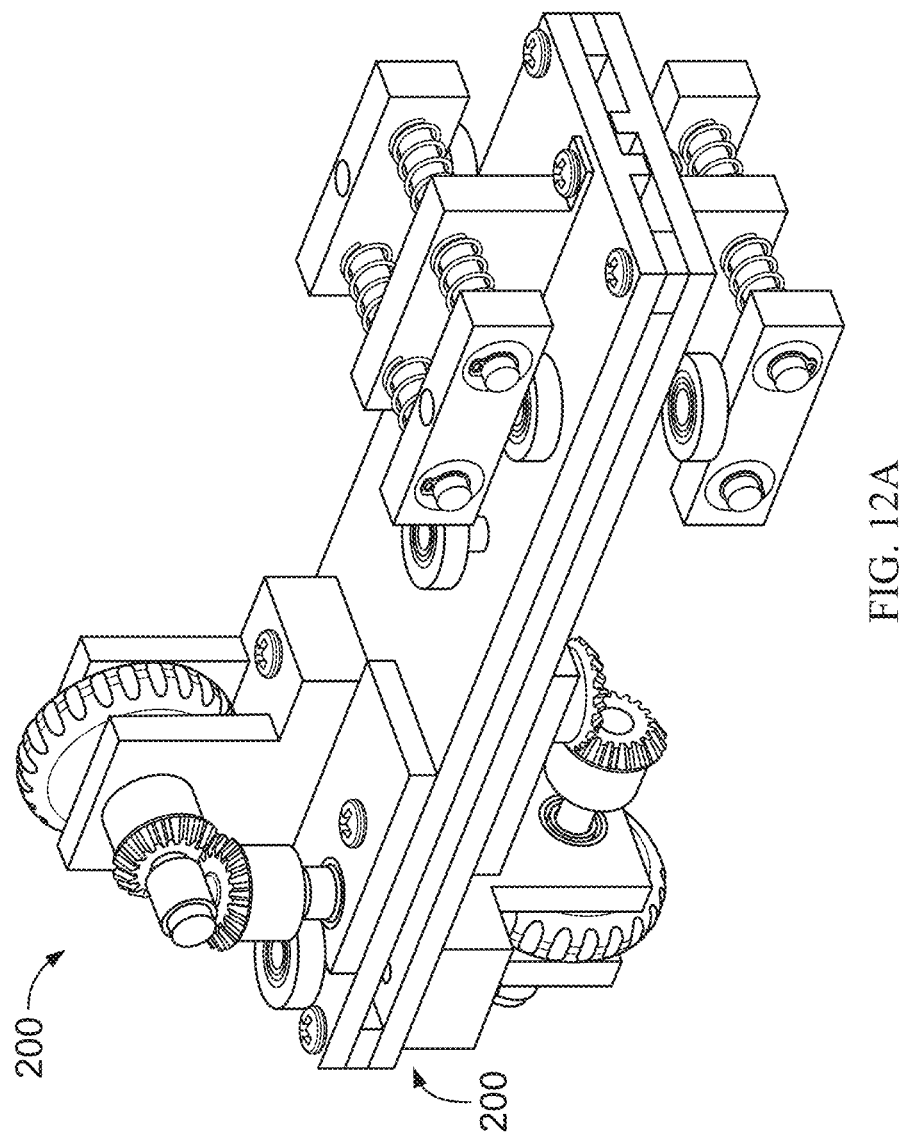
FIG. 12A is an isometric view that illustrates an arrangement of two internal mechanisms for actuation of the strings with two DOF, according to an embodiment.
Figure 12B:
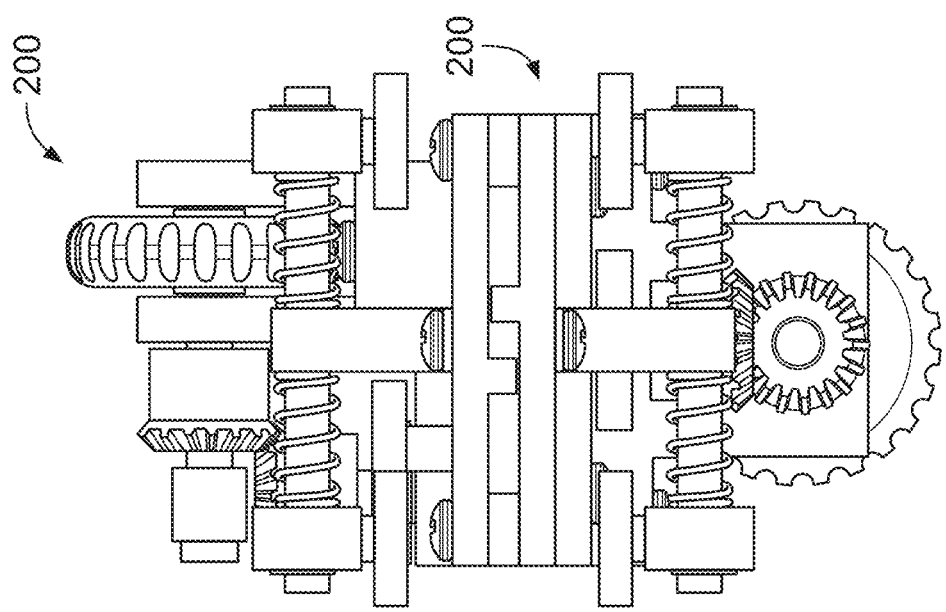
FIG. 12B is a front side view that illustrates an arrangement of two internal mechanisms for actuation of the strings with two DOF, according to an embodiment.

An embodiment having an arrangement of two such internal mechanisms 200 for controlling two independent strings 126 is shown in FIGS. 12A and 12B.

In some embodiments, handle 110 also houses a circuit board, that contains all the necessary electronics and embedded systems to capture the position of the encoders and transmit that information to a host computer through a port (e.g. USB) or wirelessly.

Figure 13A:
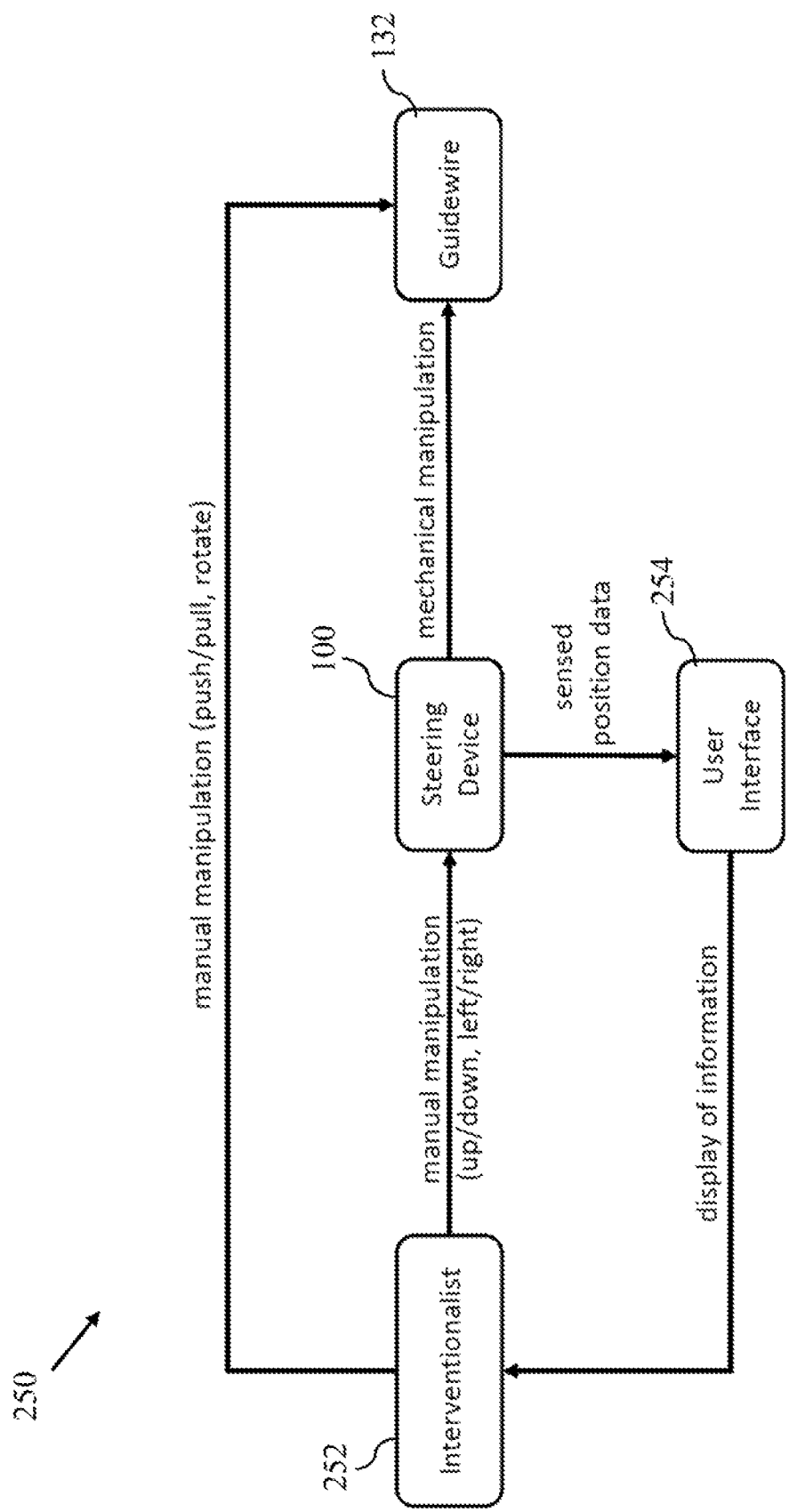
FIG. 13A is a flowchart of a system for steering and navigating the device, according to embodiments.

FIG. 13A depicts a system 250 for steering a catheter or guidewire 132 according to an embodiment. As indicated, a user, such as an interventionalist 252, can manipulate the catheter or guidewire 132 with seven DOF. The user can push/pull and rotate (two DOF) the guidewire by manipulating it remotely from the section outside the catheter handle 110. The outer sheath 122 that supports the catheter can be manipulated itself with three DOF (Push/Pull, rotation and deflection of distal end) and the two extra DOFs are provided by the steering mechanism of the expandable structure 112 as described previously. The latter two DOF, i.e., up/down and left/right, can be manipulated by the user with the aid of a user interface 254 which displays position data of the guidewire 132 or catheter tip.

Figures 13B, 13C:
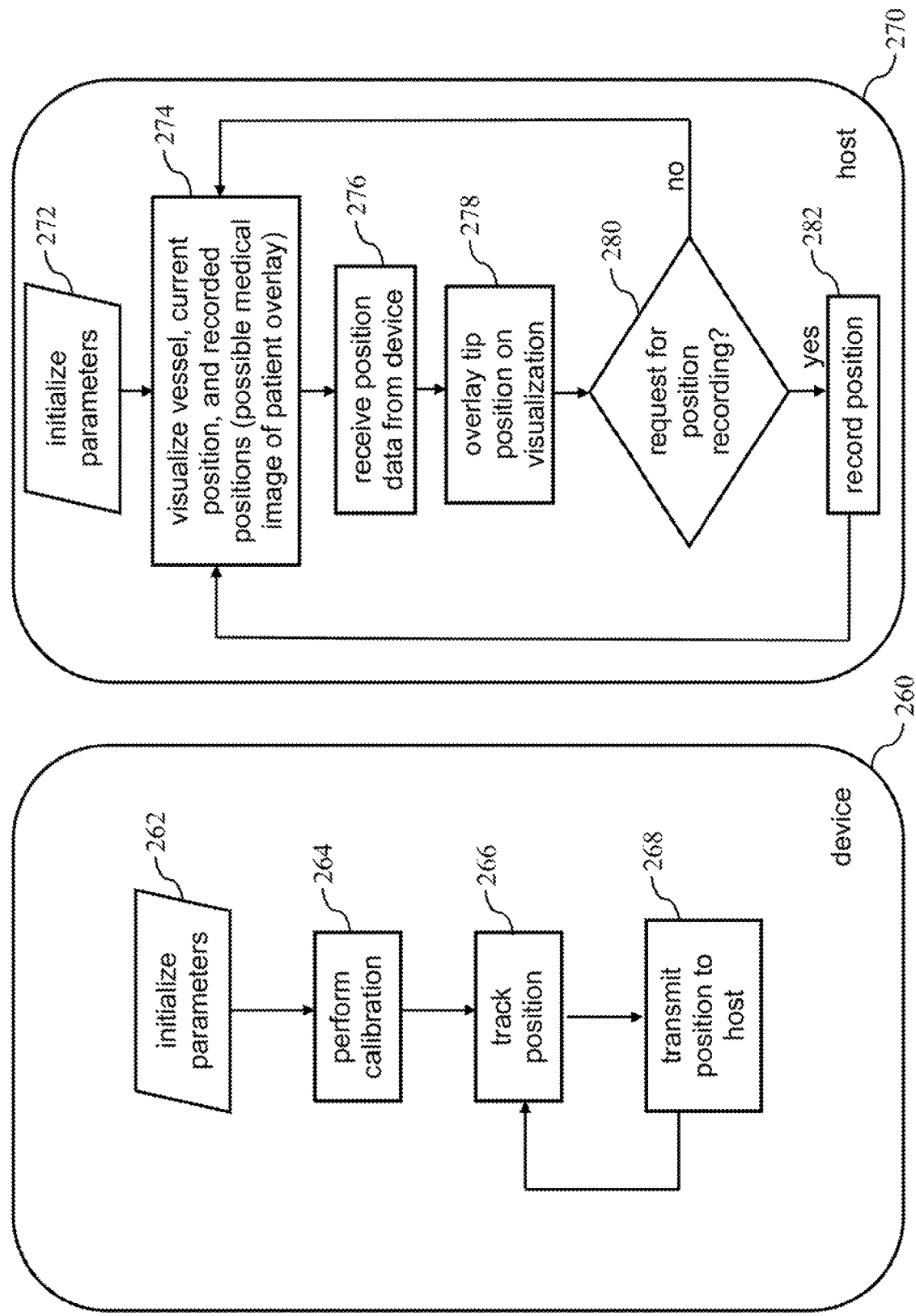
FIG. 13B is a flowchart of a program for steering and tracking the device, according to embodiments.
FIG. 13C is a flowchart of a program for steering and tracking a device such as a guidewire or catheter as implemented on a host computer, according to embodiments.

FIGS. 13B-13C are flowcharts 260 and 270, respectively, of a program which can run on an embedded system in the device 100 and on a host computer. According to FIG. 13B, the code for the embedded system on the device 100 (e.g. a microcontroller-based circuit), is primarily in charge of measuring the encoder values and transmitting them to a host computer. According to FIG. 13C, the host computer software is in charge of visualizing the position of the device 100 relative to a virtual vessel. The position of the guidewire 132 is captured in real-time and overlaid on the virtual vessel map and visualized for the user.

Flow chart 260 generally consists of steps with respect to the device 100. It includes initializing parameters at step 262, followed by performing calibration at 264, then tracking position(s) at 266, and transmitting the position(s) to the host at 268. The method cycles back to tracking further positions at 266.

Flow chart 270 generally consists of steps with respect to a host computer. It includes initializing parameters at step 272, followed by visualizing the vessel, current position, and recorded positions at step 274. This may include a medical image overlay of the patient. Next, at 276 the host receives position data from the device 100, followed by overlaying tip position on the visualization at 278, and finally an inquiry as to whether there is a request for a position recording at 280. If no request is made at 280, the method returns to step 274. If a request is made at 280, the host records the position at 282 before cycling back to step 274.

In embodiments, the user recorded positions can also be captured and visualized for the user (e.g. with different colors). Further, the user recorded positions can indicate the positions that the guidewire has been previously to indicate previous locations of interest. In some embodiments, the virtual vessel map may be augmented by an overlay of registered patient data, that may be obtained during or prior to a procedure. For example, such images may be acquired using Magnetic Resonance Imaging or X-ray computed Tomography and registered and overlaid on the virtual map based on the corresponding position of the device's distal end within the patient anatomy.

Figure 14A:
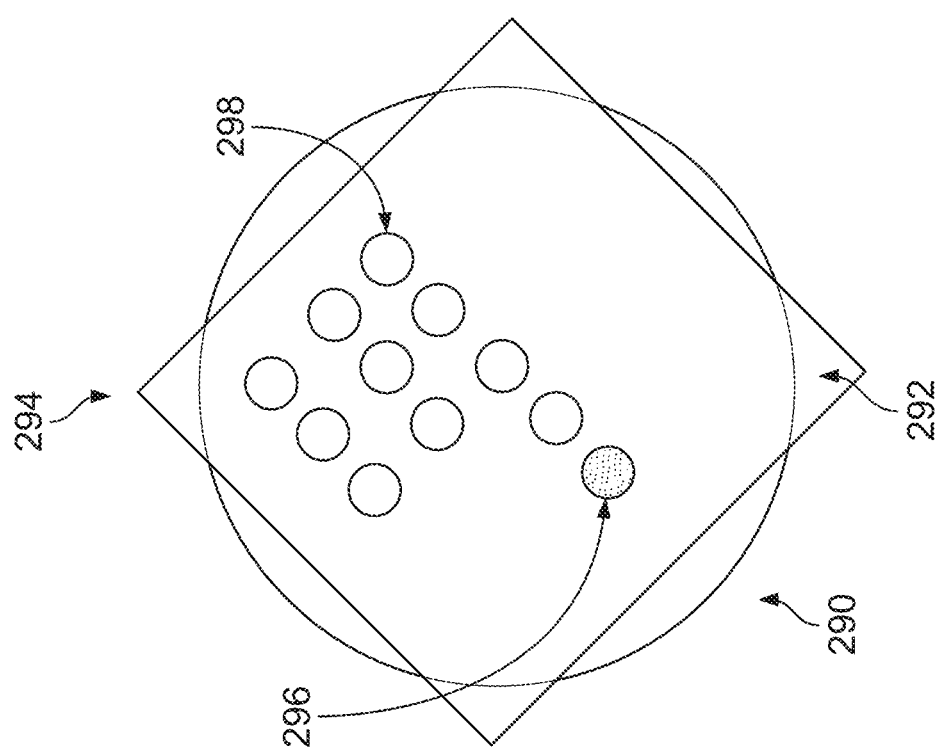
FIGS. 14A and 14B are visualizations of a virtual vessel map displayed on a graphical user interface, according to embodiments.
Figure 14B:
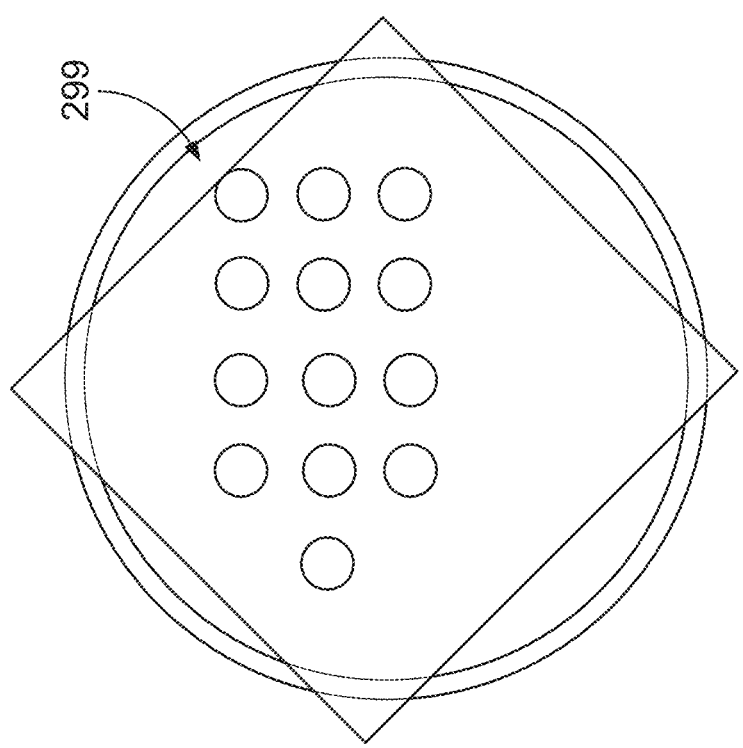

FIGS. 14A and 14B depict an example of a virtual vessel map displayed on a graphical user interface. In embodiments, a circle 290 represents the vessel lumen. A square 292 represents the workspace of the steering device and corners 294 of the square represent the anchor points of branches 120. A dark dot 296 represents the current position of the tip or eyelet 128. Dark dot 296 can be continuously updated in real time. A plurality of lighter dots 298 represent the previous positions of the tip or eyelet 128 that have been recorded. A medical image (e.g. MRI) overlay 299 on the visual interface is depicted in FIG. 14B. In this example image, the dark locations on the image are the openings within an occlusion which is the hypothetical target for guidewire tip navigation. In an embodiment, the display may be mounted directly on handle 110 (e.g., LCD or LED screen) or may comprise a number of discrete light-emitting diodes arranged to represent the device's workspace and with different colors of LEDs being used to represent the previous and current positions of the device.

Figure 15:
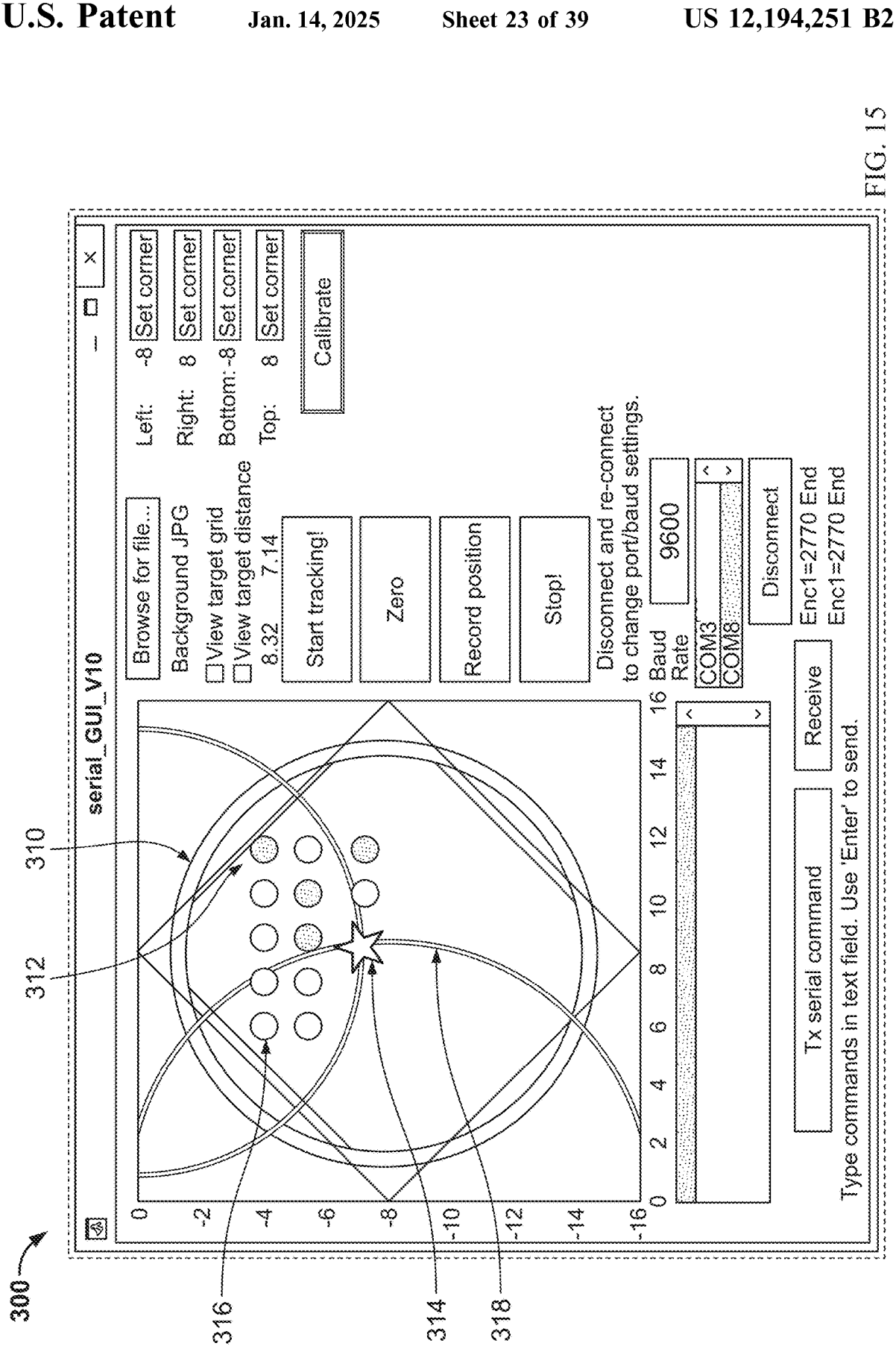
FIG. 15 illustrates a user interface demonstrating the obtained images, showing the immediate and past positions of the device relative to a navigation map displayed on a graphical user interface, according to embodiments.

FIG. 15 depicts an example of a graphical user interface 300. In embodiments, a circular shape 310 virtually represents the vessel lumen. A rectangle 312 represents the workspace of the steering device 100 and corners of the rectangle represent the anchor points 124 of the branches. A star 314 represents the current position of the tip or eyelet 128 which is updated in real-time. The arcs 318 represent the length of the strings that have been tracked and their intersection estimates the current position of the eyelet 128 that is represented by 314. Dark dots 316 represent previous locations of interest that have been recorded by the user.

Figure 16B:
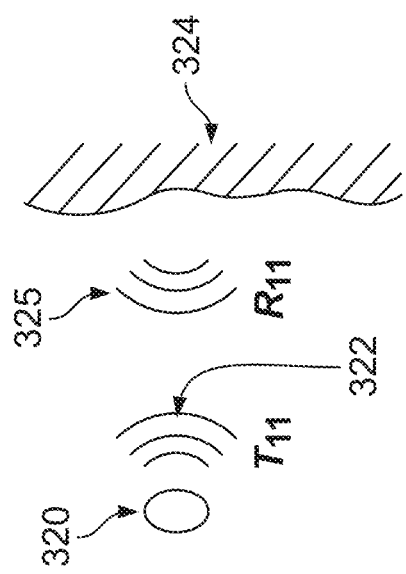
Figure 16C:
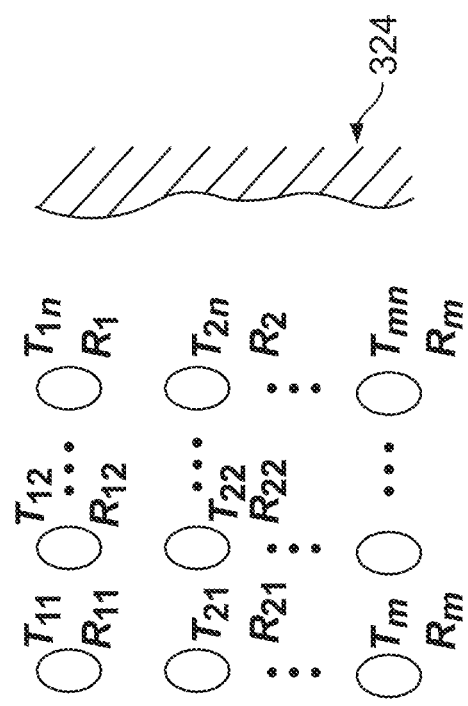

FIGS. 16A, 16B and 16C collectively depict the concept for utilizing the proposed device for the purpose of imaging. In an embodiment, eyelet 128 containing the sensor 134 and/or transmitter can be moved to a different location 320 and at each location a transmission, such as an ultrasound burst of signal 322, can be transmitted and reflected from a target tissue of interest 324. The reflected signal 325 can then be picked up by the sensor 134. By moving the eyelet 128 containing the sensor/transmitter to different locations, such as 320, a desired area of interest can be scanned, and measurements can be obtained for the purpose of reconstructing an image such as 3D ultrasound image. As shown in these figures, transmitter signals are noted as T11-Tmn and represent transmitter signals at various arrayed locations. Likewise, reflected signals shown in these figures are noted as R11-Rmn and represent reflected signals at various corresponding arrayed locations as well.

Figure 17A:
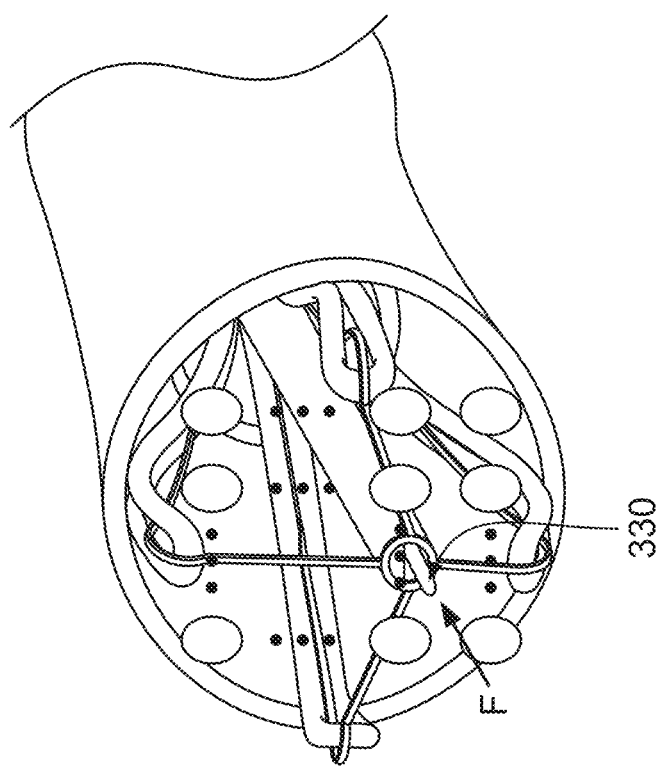
FIGS. 17A-C demonstrate the concept of using the steering mechanism for acquiring measurements at multiple known positions using an independent device in order to obtain an image of the anatomy of interest, according to an embodiment.
Figure 17B:
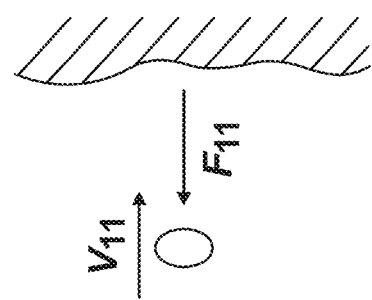
Figure 17C:
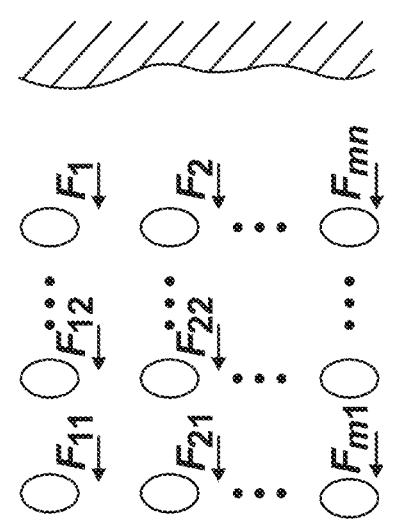

In an embodiment, as depicted in FIGS. 17A, 17B, and 17C, an independent device may be inserted into the internal catheter 130. This device may be equipped with a transceiver or sensor 330. In an embodiment, this sensor 330 may be a force sensor and may be used to apply a known mechanical excitation to the tissue of interest to obtain a mechanical response that can be measured with the sensor 330. By scanning and moving the eyelet 128, and therefore the sensor 330 to different locations, a desired area of interest can be scanned, and measurements can be obtained for imaging (e.g. elastography). As shown in these figures, the known mechanical excitation is noted as V11, and likewise, indications F11-Fmn denote mechanical responses at various arrayed locations.

Figures 18A, 18B:
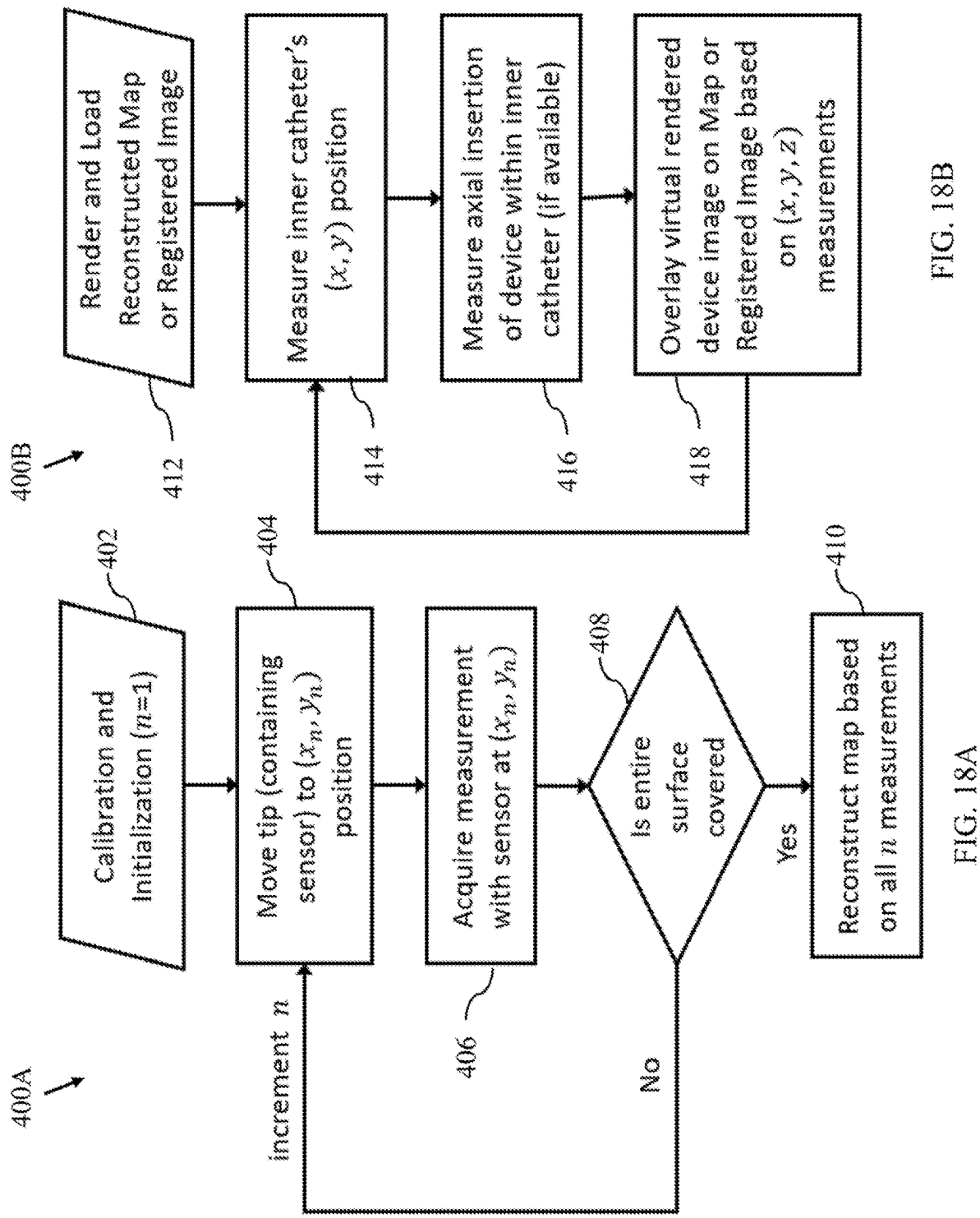
FIG. 18A is a flowchart of a program for obtaining an image of a target, according to an embodiment.
FIG. 18B is a flowchart of a program for a navigation platform and the corresponding user interface, according to an embodiment.

FIGS. 18A and 18B describe flowchart 400A and 400B of a program which can run on an embedded system in the device and on a host computer. According to FIG. 18A, the known positions of the device can be used to cover and obtain measurements from a complete surface of interest. In an embodiment, the position of the device can be moved by the user manually or alternatively automatically by actuators coupled to the mechanisms within the handle 110. FIG. 18B describes a flowchart of a software that can be run on the embedded system in the device and on the host computer. The software describes how the device's known position together with potentially other measurements, such as measurements from sensors 134 at the tip of the device and/or a sensor tracking the insertion length of a desired device of interest, such as a guidewire 132, within the internal catheter 130 can be used to provide a virtual 3D visualization of the tip of the guidewire 132 relative to the branches 124 and within the device's workspace. Such information may be overlaid on images constructed based on methods described previously and in the flowchart of FIG. 18A.

Flowchart 400A generally consists of calibration and initialization (n=1) at 402, followed by moving the tip (containing a sensor) to a position $(x_n, y_n)$ at 404. The next step 406 relates to acquiring a measurement with a sensor at $(x_n, y_n)$. Next at 408 the system checks whether the entire surface is covered. If not, the method cycles to step 404. If yes, the method proceeds to reconstructing the map based on all n measurements at 410.

Flowchart 400B generally consists of rendering and loading the reconstructed map or registered image at 412 followed by measuring the inner catheter's (x, y) position at 414. Next at 416 is measuring axial insertion of the device 100 within the inner catheter, if available. Finally, at 418 is overlaying the virtual rendered device image on the map or registered image based on (x, y, z) measurements.

Accordingly, methods for positioning and tracking a device 100 within a vessel lumen or cardiac chamber of a patient can be understood. Some methods required providing an electromechanical steering device system that guides the guidewire 132 or interventional device. A electromechanical steering device system can include: a catheter 132 with expandable branches 120 and a eyelet 128 at its distal tip that is controlled by a set of strings 126 actuated by a handle 110. The system may also include a plurality of sensors attached to one or more of: the interventional device, the catheter 132, and the set of strings 126; and a computing device communicatively coupled with the plurality of sensors. A computing device can include: at least one processor and memory operably coupled to the at least one processor and configured to store instructions invoked by the at least one processor and a positioning and tracking engine configured for tracking interventional device position and communications for rendering and visualization of images; and a GUI display communicatively coupled with the computing device. Methods can includes moving a tip of an interventional device to a desired position(s) by actuating the handle 110. The methods can include acquiring measurements from the plurality of sensors at the desired position(s). Methods can further include reconstructing a map of the vessel lumen or cardiac chamber of interest based on the acquired measurements. Methods also can include rendering and loading a virtual rendered device image using the position and tracking engine. Methods can also include measuring the catheter position from the plurality of sensors and measuring the axial insertion of the interventional device within the catheter from the plurality of sensors. Finally, some methods further include overlaying the virtual rendered device image on the map based on the measurements in an overlaid image presented on the GUI display.

FIG. 19A depicts the expandable structure positioned inside a stent graft 420 that is deployed within an abdominal aortic aneurysm 422 and suggests how the device may be used as part of the treatment procedure. Using the steering device 100, the guidewire 132 can be navigated for the purposes of navigating towards the branches or openings of the stent 424 to connect the main stent 420 to the branched arteries such as the renal arteries 426 for gate cannulation purposes.

FIG. 19A depicts the expandable structured positioned inside a stent graft 420 that is deployed within an abdominal aortic aneurysm 422 and suggests how the device may be used as part of the treatment procedure. Using the steering device 100, the guidewire 132 can be navigated for the purposes of navigating towards the branches or openings of the stent 424 to connect the main stent 420 to the branched arteries such as the renal arteries 426 for gate cannulation purposes.

Figure 19B:
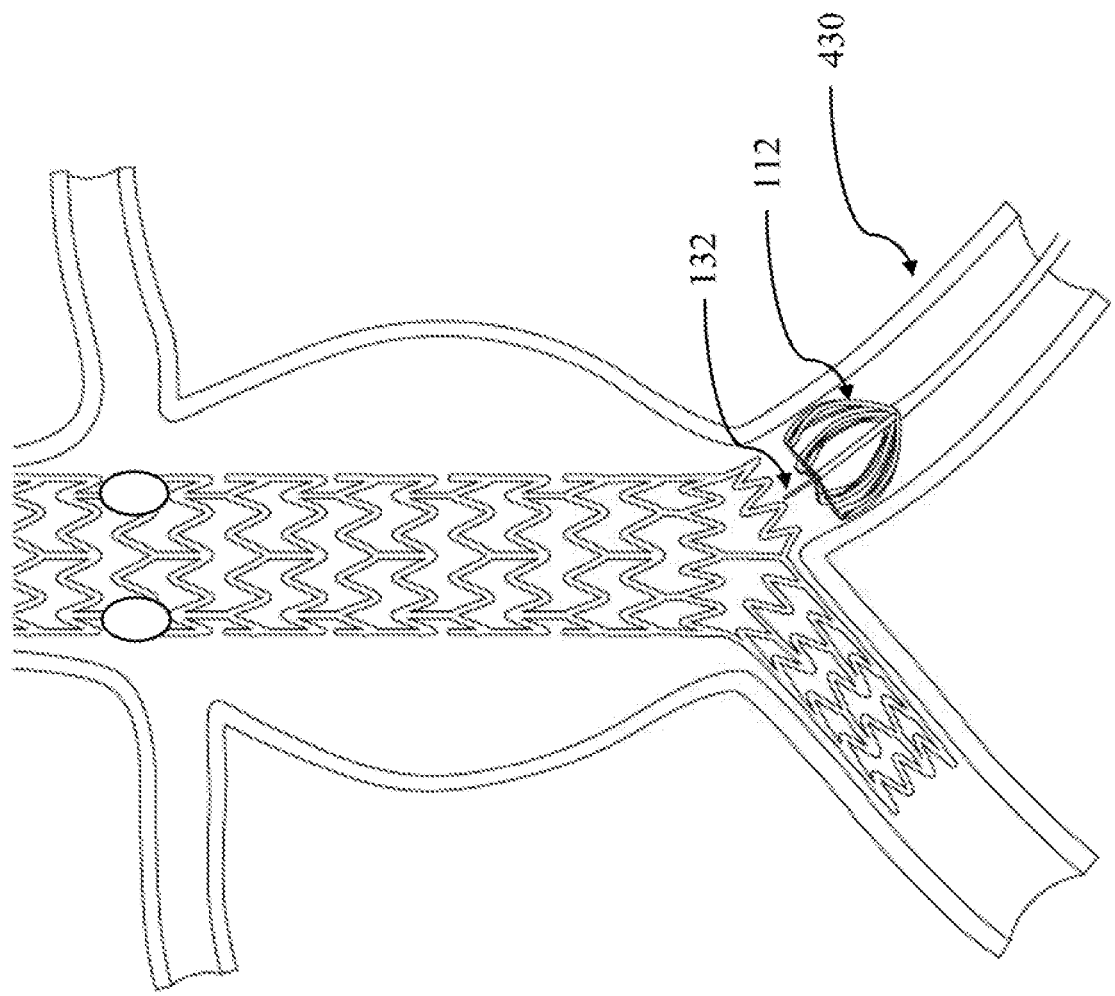
FIG. 19B demonstrates a potential approach for use of the device for gate cannulation in EVAR, according to an embodiment.

FIG. 19B suggests an alternative application of the steering device 100 and possible position of deployment for the purposes of gate cannulation as part of an endovascular abdominal aortic aneurysm repair procedure. In this setup, the expandable structure 112 is positioned close to the opening of the superior femoral artery 430 and is used to navigate the guidewire 132 to the purposes of gate cannulation.

Figure 20:
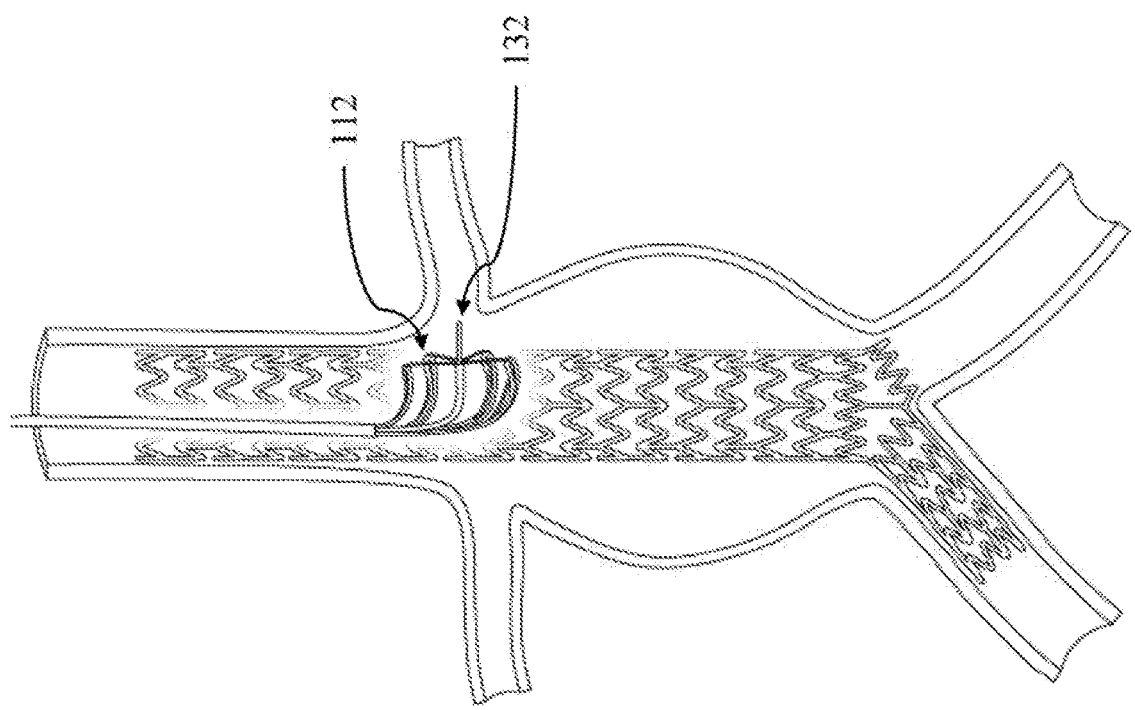
FIG. 20 demonstrates an alternative embodiment for the tip mechanism with the expandable distal structure taking a specific desired shape upon deployment for serving the specific objective, according to an embodiment.

FIG. 20 illustrates an alternative embodiment for the expandable structure 112. As shown, the structure can be formed constructed such that when it is advanced out of the sheath 122 or deployed, it orients itself in a specific direction that may facilitate the specific intervention, such as gate cannulation for EVAR procedures.

Figure 21:
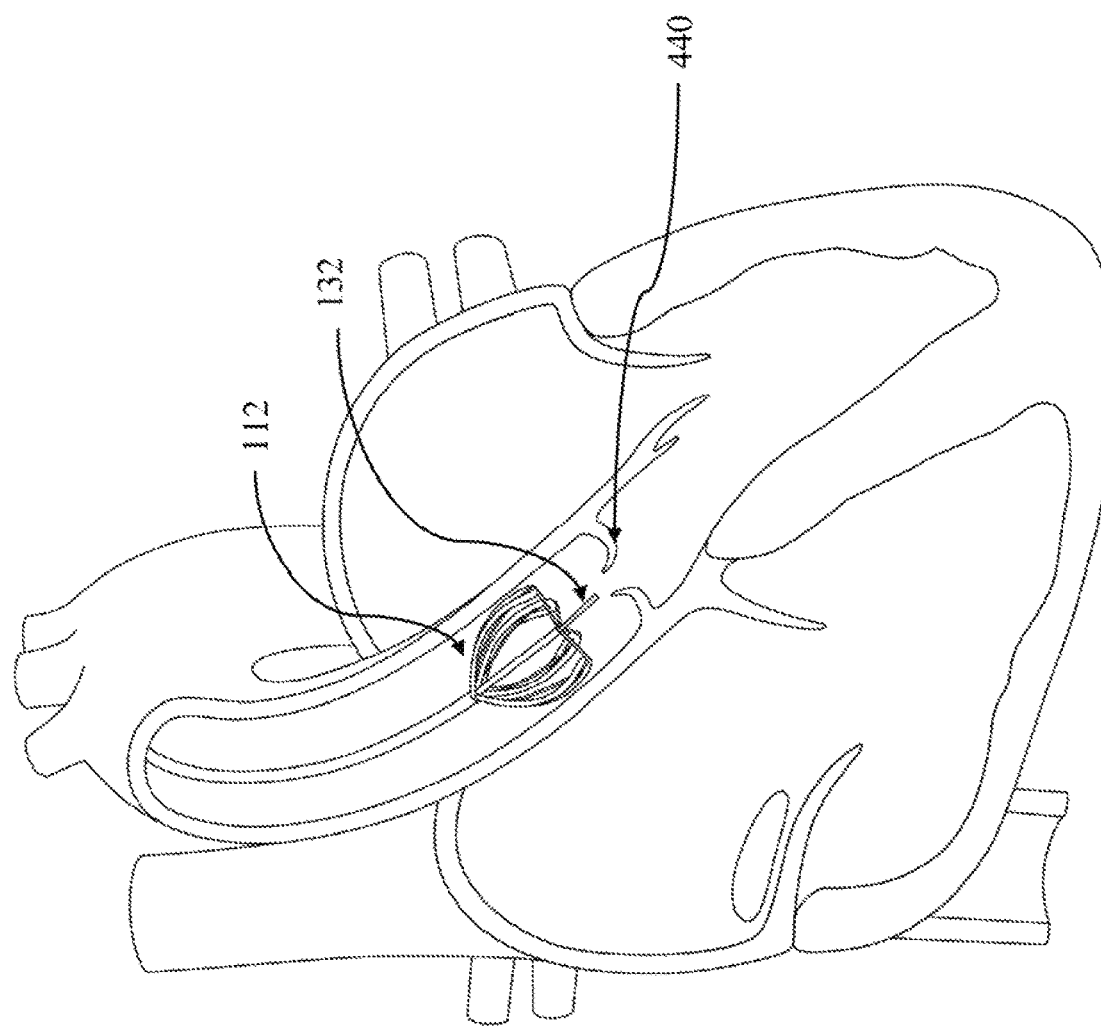
FIG. 21 demonstrates a potential approach for use and deployment of the device for facilitating guidewire navigation for transaortic valve implantation procedures, according to an embodiment.

FIG. 21 illustrates the expandable structure 112 positioned within the aorta for facilitating the navigation of a guidewire/catheter for crossing the aortic valve 440 and suggests an application as part of transcatheter aortic valve implantation.

Figure 22A:
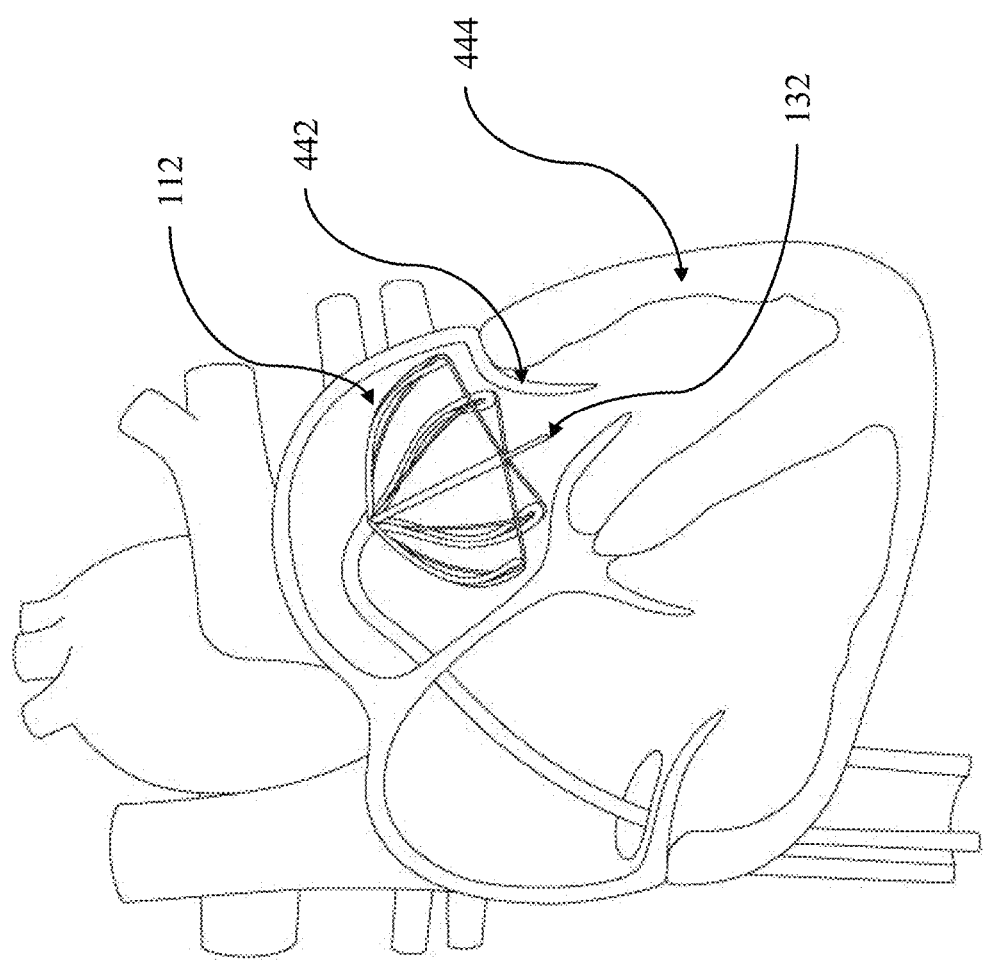
FIG. 22A demonstrates a potential approach for use and deployment for facilitating guidewire navigation for mitral valve implantation of left ventricle catheterization procedures, according to an embodiment.

FIG. 22A shows the expandable structure 112 positioned in the left atrium for the purposes of navigating a guidewire or catheter as part of mitral valve 442 implantation procedure or for the purposes of performing a catheterization procedure in left ventricle 444.

Figure 22B:
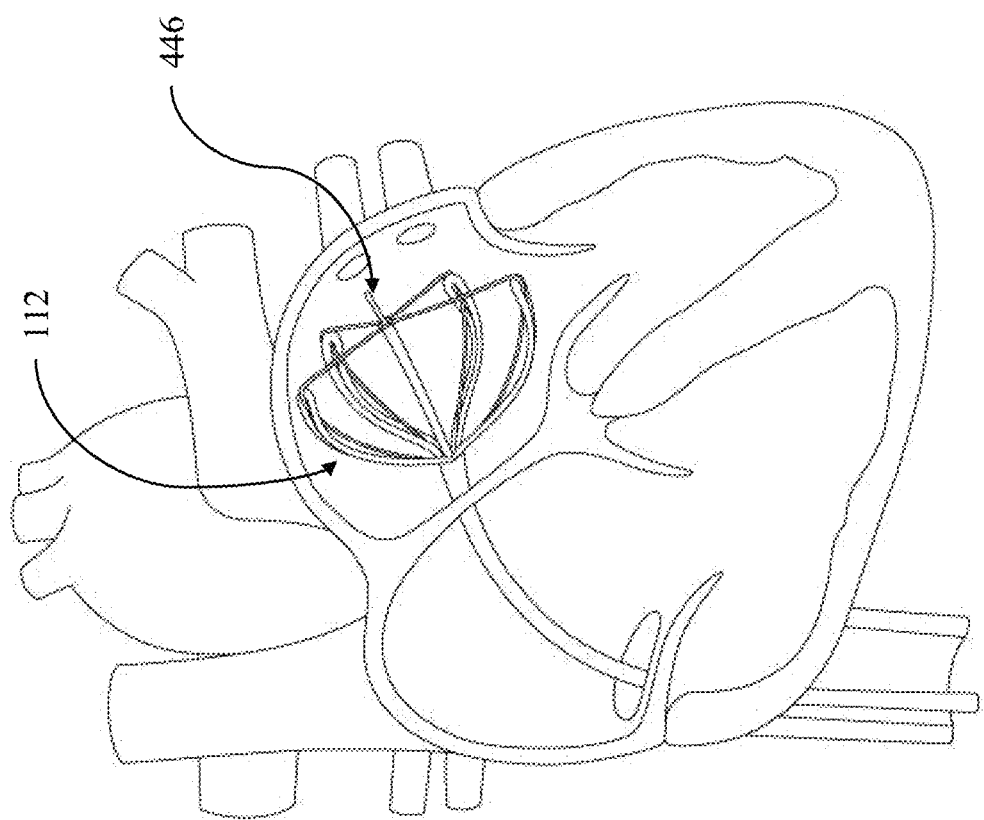
FIG. 22B demonstrates a potential approach for use and deployment for ablation in the left atrium for the treatment of diseases such as atrial fibrillation, according to an embodiment.

FIG. 22B shows the expandable structure 112 positioned in the left atrium. As an example, in cardiac catheterization procedure for the treatment of atrial fibrillation, the steering device may be used to position, track and navigate an ablation catheter 446 at the desired target locations.

Figure 23:
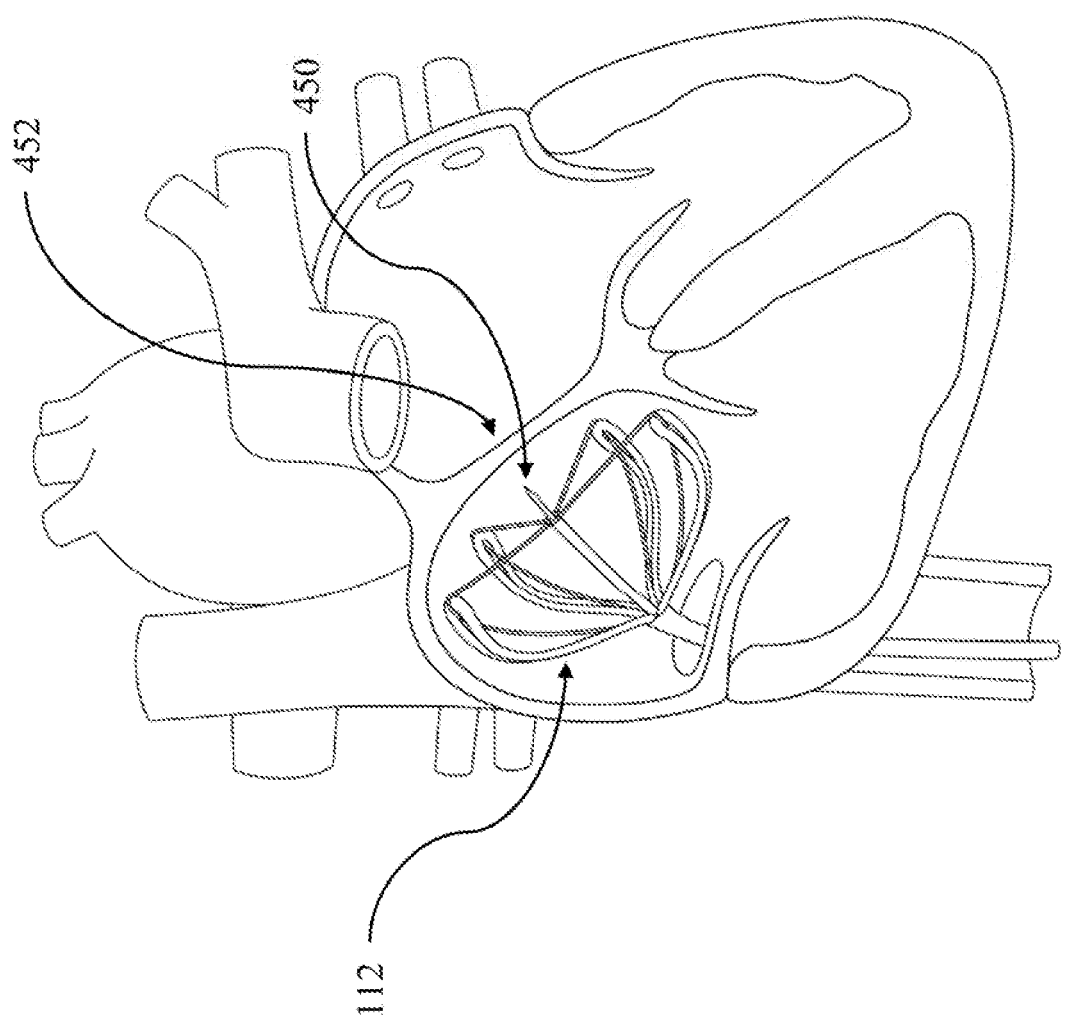
FIG. 23 demonstrates a potential approach for use and deployment for navigation of a needle for interatrial transseptal puncture, according to an embodiment.

FIG. 23 depicts the expandable structure 112 deployed in the right atrium for the purposes of navigation of a needle 450 for accurate and reliable interatrial membrane 452 transseptal puncture.

Figure 24:
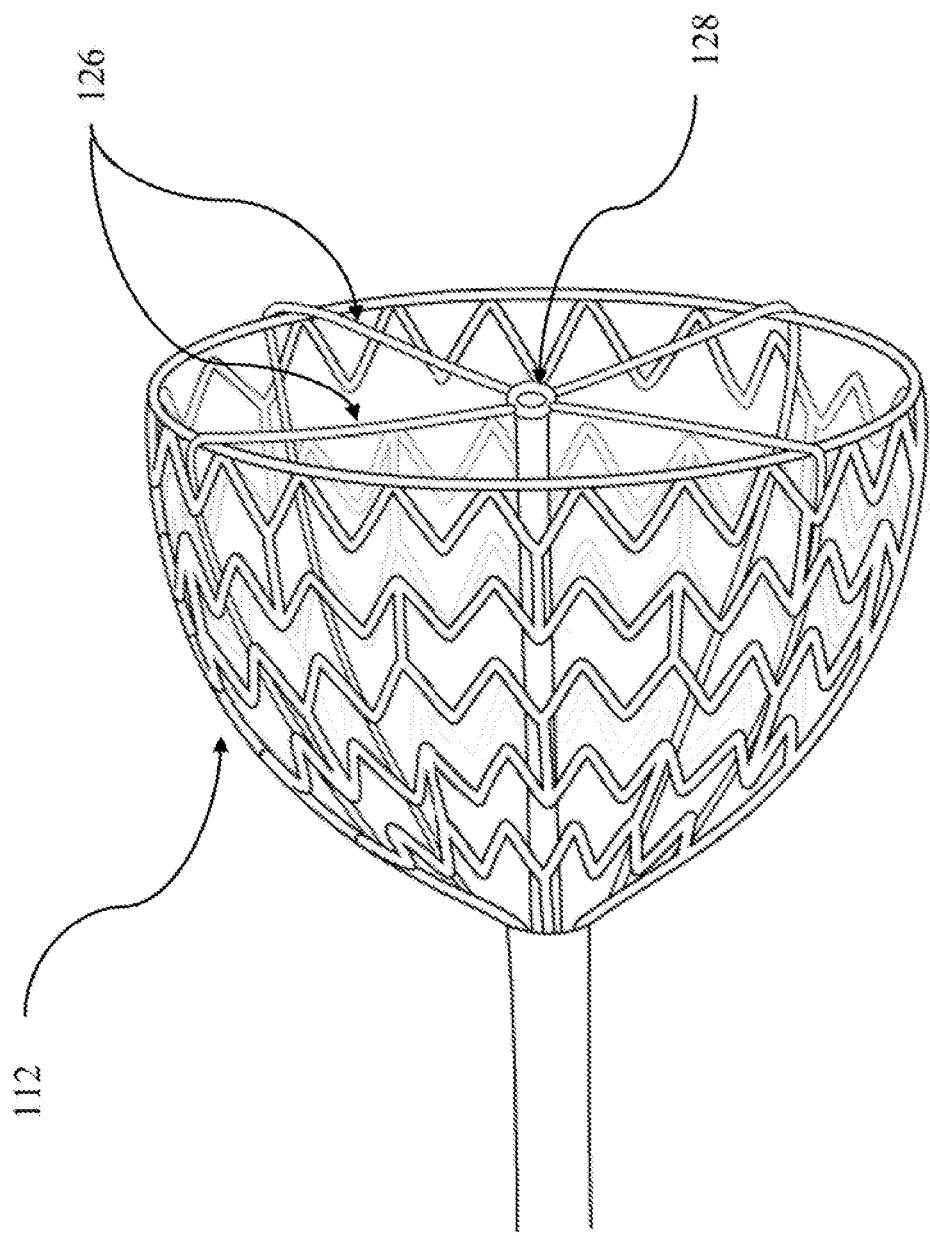
FIG. 24 demonstrates a version of the expandable distal tip structure and mechanism according to an alternative embodiment, according to an embodiment.

FIG. 24 depicts an alternative embodiment for the expandable structure 112 where a mesh like structure is used for expansion and support of the strings 126 to permit the steering and navigation of the internal catheter and its eyelet 128 or tip.

Figure 25:
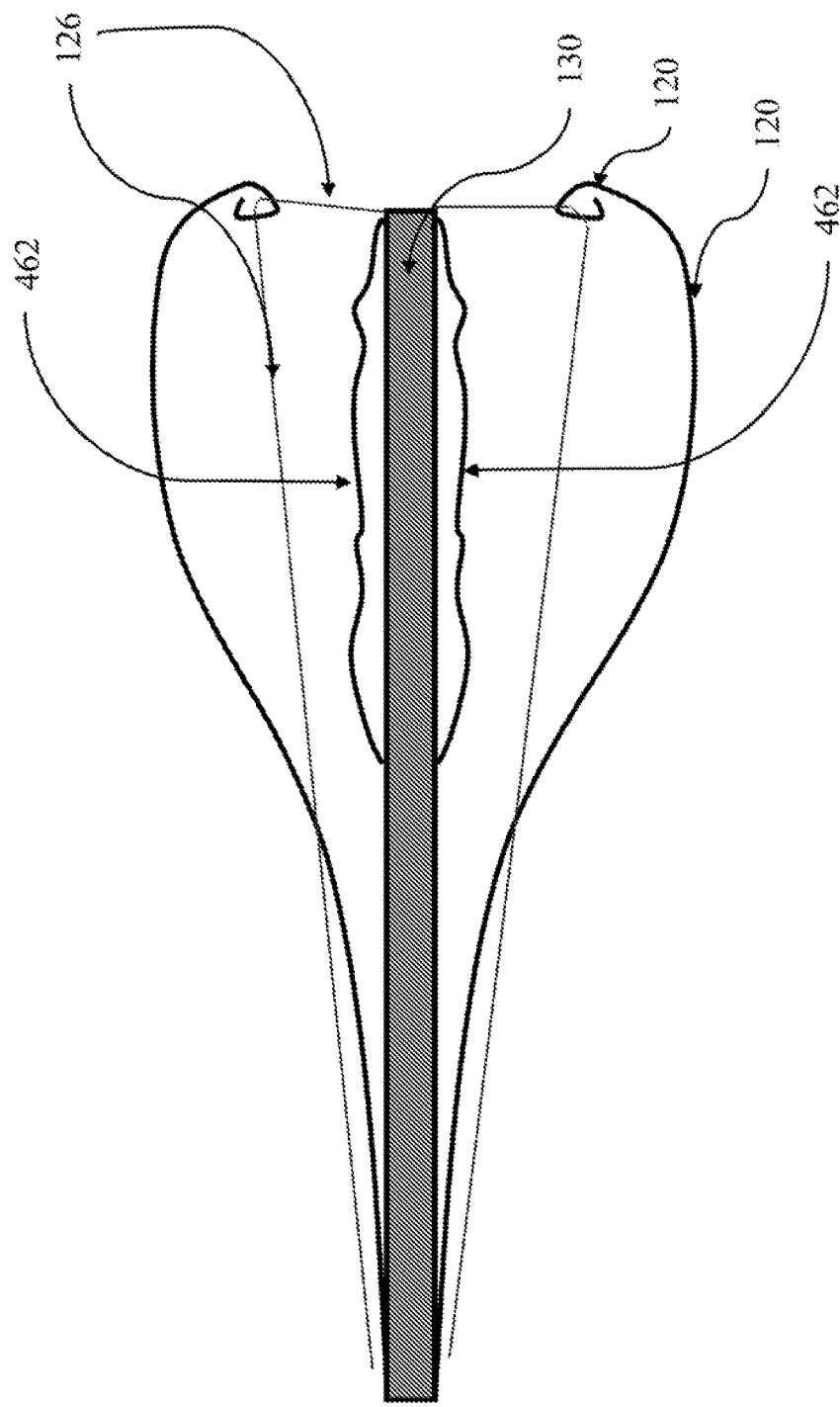
FIG. 25 demonstrates a side view of an embodiment of the tip mechanism utilizing an inflatable structure, or balloon, for opening and supporting the expandable structure, according to an embodiment.

FIG. 25 depicts a sideview of an alternative embodiment for the expandable structure 112. As it is illustrated in this embodiment, a balloon 462 may be connected to internal catheter 130. The channels for the balloon 462 may run along the length of internal catheter 130. The balloon 462 may be inflated, and their inflation will apply pressure onto the expandable structure or the branches 120 according to an embodiment. This mechanism may be used to expand the self-expanding structure, when it is not able to do it on itself relying only on the material mechanical properties.

In an alternative embodiment, two sets of steering mechanisms can be used at different positions along the length of the device to allow for bending of the guidewire as well as its positioning. In such an embodiment, a second steering mechanism, similar to the one shown in FIGS. 2 and 3, could be integrated into the device at a fixed, or variable, offset from the first steering mechanism. By controlling each steering mechanism independently and depending on the distance between the two eyelets where the guidewire passes, the bending of the guidewire and its position may be controlled simultaneously.

In yet another alternative embodiment, an imaging device, such as an ultrasonic transducer could be connected to the steered section of eyelet 128 to allow for tracking the position of the imaging device for volumetric image reconstructions (e.g. 2D ultrasound from 1 ultrasound transducer). In another embodiment, an imaging probe, such as an array of ultrasonic transducers, or optical imaging devices, can be connected to the sheath or branches 120, to allow for imaging the anatomy, simultaneously to guidewire or catheter navigation and tracking.

In yet another alternative embodiment, various imaging sensors, or combinations thereof, such as an optical sensor, ultrasound sensor/transducer, a radioactivity detector, scintillator, photomultiplier, radiofrequency antenna, with a collimator or filter or combination thereof may be used as a sensor 134. In another embodiment, a laser source may be positioned within the internal catheter 130 to provide means of delivering therapy at known desired targets based on obtained tracking information with or without image information obtained with the device.

In other embodiments, the actuation method for steering may be electromagnetic instead of mechanical (i.e. strings 126). In such an embodiment, an electric field or magnetic field generator (e.g. coil) may be connected to the branches 120 or to eyelet 128 to generate relative force between the branches and the steered opening to allow for positioning of the eyelet relative to the branches. In an alternative embodiment, the strings may be replaced with nitinol wire which may be expanded and retracted using electric current to control the position of the eyelet 128.

In an embodiment, the sheath 122 would be steerable and another string connected to the tip of sheath 122 would be actuated (i.e. pulled) in the handle to allow for another degree of freedom in steering and navigation of sheath 122.

In alternative embodiments, there may be one, two, or three strings 126 that are used for steering the internal catheter 130.

In an alternative embodiment, a balloon may be integrated into the internal catheter and it may be inflated and used to anchor the internal catheter 130 relative to the anatomy as desired.

In an embodiment the wheels 142, 144 on the device handle 110 can be pressed, or clicked by the user to allow interaction with the graphical user interface for applications such as recording the current position of interest.

Devices, systems and methods described herein can be used in various applications. For example, the described system can be used for navigation of guidewires for angioplasty procedures. In one application, the above system can be used for navigation of guidewires in EVAR or transcatheter aortic valve implantation (TAVI). In one application, the above system can be used for navigation of catheters in catheterization procedures (e.g. cardiac ablation or cryoablation, or lead placement) or for positioning needles for trans-septal puncture in cardiac catheterization procedures. In yet another example, the above system can be used to manipulate and navigate a drug delivery catheter (e.g. injection needle) for targeted delivery of drugs or stems cells in cardiac therapy in a systematic and controllable approach. In yet another example, the proposed systems and methods can be used for biopsy or delivery of therapy for applications in oncology (e.g. lung biopsy or colonoscopy).

Devices, systems, and methods disclosed herein provide catheter and guidewire steering capability without modification of the guidewires or catheters. The proposed approach also allows for accurately tracking the position of the guidewire, or catheter, and therefore allows for its visualization with respect to the vessel lumen, or cardiac chamber. This invention allows for accurate 5-DOF continuous position control of the guidewire or catheter. This novel approach provides two extra DOF in motion control relative to conventional guidewire or catheter manipulation techniques together with unique features that permit accurate local position control and tracking ability as well as support and anchoring.

In embodiments, the devices disclosed herein and/or their components or systems include computing devices, microprocessors and other computer or computing devices, which can be any programmable device that accepts digital data as input, is configured to process the input according to instructions or algorithms, and provides results as outputs. In an embodiment, computing and other such devices discussed herein can be, comprise, contain or be coupled to a central processing unit (CPU) configured to carry out the instructions of a computer program. Computing and other such devices discussed herein are therefore configured to perform basic arithmetical, logical, and input/output operations.

Computing and other devices discussed herein can include memory. Memory can comprise volatile or non-volatile memory as required by the coupled computing device or processor to not only provide space to execute the instructions or algorithms, but to provide the space to store the instructions themselves. In embodiments, volatile memory can include random access memory (RAM), dynamic random access memory (DRAM), or static random access memory (SRAM), for example. In embodiments, non-volatile memory can include read-only memory, flash memory, ferroelectric RAM, hard disk, floppy disk, magnetic tape, or optical disc storage, for example. The foregoing lists in no way limit the type of memory that can be used, as these embodiments are given only by way of example and are not intended to limit the scope of the invention.

In embodiments, the system or components thereof can comprise or include various engines, each of which is constructed, programmed, configured, or otherwise adapted, to autonomously carry out a function or set of functions. The term "engine" as used herein is defined as a real-world device, component, or arrangement of components implemented using hardware, such as by an application specific integrated circuit (ASIC) or field-programmable gate array (FPGA), for example, or as a combination of hardware and software, such as by a microprocessor system and a set of program instructions that adapt the engine to implement the particular functionality, which (while being executed) transform the microprocessor system into a special-purpose device. An engine can also be implemented as a combination of the two, with certain functions facilitated by hardware alone, and other functions facilitated by a combination of hardware and software. In certain implementations, at least a portion, and in some cases, all, of an engine can be executed on the processor(s) of one or more computing platforms that are made up of hardware (e.g., one or more processors, data storage devices such as memory or drive storage, input/output facilities such as network interface devices, video devices, keyboard, mouse or touchscreen devices, etc.) that execute an operating system, system programs, and application programs, while also implementing the engine using multitasking, multithreading, distributed (e.g., cluster, peer-peer, cloud, etc.) processing where appropriate, or other such techniques. Accordingly, each engine can be realized in a variety of physically realizable configurations, and should generally not be limited to any particular implementation exemplified herein, unless such limitations are expressly called out. In addition, an engine can itself be composed of more than one sub-engines, each of which can be regarded as an engine in its own right. Moreover, in the embodiments described herein, each of the various engines corresponds to a defined autonomous functionality; however, it should be understood that in other contemplated embodiments, each functionality can be distributed to more than one engine. Likewise, in other contemplated embodiments, multiple defined functionalities may be implemented by a single engine that performs those multiple functions, possibly alongside other functions, or distributed differently among a set of engines than specifically illustrated in the examples herein.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A steering device for positioning an interventional device within a vessel lumen or cardiac chamber of a patient, comprising:
  a set of expandable structures, including separate distal end branches, that can be controlled to spread out within the vessel lumen or cardiac chamber and apply circumferential forces to surrounding tissue;
  a set of strings, comprising all strings present in the steering device, each string slidably anchored to a different one of the separate distal end branches of the set of expandable structures;
  an eyelet, having a ring-shaped perimeter and a central opening, surrounded by the set of expandable structures and supported by distal ends of the set of strings, the set of strings are secured around the ring-shaped perimeter of the eyelet, the eyelet configured to permit the interventional device to pass through the central opening;
  wherein the set of strings is configured to manipulate the eyelet with two degrees of freedom and—permit control of the position of the interventional device in a geometrically-defined area relative to the vessel lumen or cardiac chamber at a location of the set of expandable structures.

2. The steering device of claim 1, wherein the interventional device is a guidewire, a catheter, or a needle.

3. The steering device of claim 1, further comprising: an internal catheter including a lumen extending the length of the internal catheter, the internal catheter being configured to initially guide the interventional device into the patient via passage through said lumen, the internal catheter having a proximal end accessible outside the patient and a distal end aligned with the ring-shaped perimeter of the eyelet.

4. The steering device of claim 3, wherein a sheath surrounds a least a portion of the internal catheter and can restrain the set of expandable structures from spreading out circumferentially.

5. The steering device of claim 3, further comprising a handle configured to manipulate the strings from the proximal end of the internal catheter.

6. The steering device of claim 5, wherein the handle permits a plurality of adjustments for steering the interventional device.

7. The steering device of claim 5, further including one or more tensioning mechanisms, that include at least one spring, located within the handle, and configured to maintain tension in the set of strings during use.

8. The steering device of claim 1, wherein encoders are mechanically coupled to the strings to track positions of the eyelet and the interventional device.

9. The steering device of claim 1, further comprising a motion sensor configured to measure positions of the interventional device.

10. A steering device for positioning an interventional device within a vessel lumen or cardiac chamber of a patient, comprising:
  an internal catheter of flexible, elongate structure having a central lumen extending between a proximal end and a distal end;
  a handle for user manipulation and steering control coupled to the proximal end of the internal catheter;
  an elongate sheath at least partially surrounding the internal catheter along the length of the internal catheter;
  a set of expandable branches located at the distal end of the internal catheter, each branch separate from one another, that can be controlled to spread out within the vessel lumen or cardiac chamber and apply circumferential forces to surrounding tissue by manipulating the set of expandable branches and the elongate sheath with respect to each other;
  a set of strings, comprising all strings present in the steering device, each string having a proximal end and a distal end, coupled to the handle at the proximal end for user manipulation via the handle, extending within the elongate sheath along the internal catheter, and engaging an anchor point of a different branch of the set of expandable branches proximal of the distal ends;

an eyelet, having a ring-shaped perimeter defining a central opening, surrounded by the set of expandable branches and supported by the distal ends of the set of strings which are secured around the ring-shaped perimeter of the eyelet, the eyelet coupled and aligned with the distal end of the internal catheter creating a passageway through the central opening of the eyelet.

11. The steering device of claim 10, wherein by manipulating the set of strings with the handle, the eyelet and corresponding portion of the interventional device passing through the eyelet are positionable in a geometrically-defined area defined by the anchor points of the expandable branches.

12. The steering device of claim 10, wherein the interventional device is a guidewire, a catheter, or a needle.

13. The steering device of claim 10, wherein encoders are mechanically coupled to the strings to track positions of the eyelet and the interventional device.

14. The steering device of claim 10, wherein the set of strings includes four strings.

15. The steering device of claim 10, further including one or more tensioning mechanisms, that include at least one spring, located within the handle, and configured to maintain tension in the set of strings during use.

16. A steering device for positioning an interventional device within a vessel lumen or cardiac chamber of a patient, comprising:

an elongate device assembly defining a central lumen extending therethrough, the assembly having a handle at a proximal end and an expandable structure at a distal end, the expandable structure comprising:

a set of expandable branches, including separate distal end branches, that can be controlled to spread out within the vessel lumen or cardiac chamber and apply circumferential force to surrounding tissue;

a set of strings, comprising all strings present in the steering device, each string slidably anchored to a different one of the separate distal end branches of the set of expandable branches;

an eyelet that is proximate the distal end of the elongate device assembly, supported by the set of strings and sized to permit passage of an interventional device through the eyelet;

wherein the set of strings is configured to manipulate the eyelet with two degrees of freedom and permit control of the position of a tip of the interventional device in a geometrically-defined area at a location of the expandable branches.

17. The steering device of claim 16, wherein the interventional device is a guidewire or a catheter.

18. The steering device of claim 16, wherein encoders are mechanically coupled to the strings to track positions of the eyelet and the interventional device.

19. The steering device of claim 16, wherein the set of strings includes four strings.

20. The steering device of claim 16, wherein the handle has a top roller, a bottom roller, and slide to steer the eyelet and extract the expandable branches.

21. The steering device of claim 16, further comprising a set of position sensors configured to measure translation of the strings and track positions of the strings relative to the expandable structure.

22. The steering device of claim 16, further including one or more tensioning mechanisms, that include at least one spring, located within the handle, and configured to maintain tension in the set of strings during use.

* * * * *